(12) United States Patent  (10) Patent No.: US 7,718,578 B2
Griffiths et al.  (45) Date of Patent: May 18, 2010

(54) METHOD OF SYNTHESIS AND TESTING OF COMBINATORIAL LIBRARIES USING MICROCAPSULES

(75) Inventors: Andrew David Griffiths, Cambridge (GB); Chris Abell, Cambridge (GB); Florian Hollfelder, Cambridge (GB); Enrico Mastrobattista, Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 11/238,257

(22) Filed: Sep. 29, 2005

(65) Prior Publication Data

US 2006/0154298 A1 Jul. 13, 2006

Related U.S. Application Data

(63) Continuation of application No. PCT/GB2004/001352, filed on Mar. 31, 2004.

(30) Foreign Application Priority Data

Mar. 31, 2003 (GB) ................................. 0307428.3

(51) Int. Cl.
C40B 30/04 (2006.01)
G12P 21/02 (2006.01)
(52) U.S. Cl. .................................. 506/23; 506/7; 506/9
(58) Field of Classification Search ................... 506/23, 506/9, 7
See application file for complete search history.

(56) References Cited

U.S. PATENT DOCUMENTS

| 5,512,131 | A | | 4/1996 | Kumar et al. |
| 5,783,431 | A | * | 7/1998 | Peterson et al. ............. 435/455 |
| 5,858,670 | A | | 1/1999 | Lam et al. |
| 5,904,933 | A | | 5/1999 | Riess et al. |
| 5,942,056 | A | | 8/1999 | Singh |
| 6,103,537 | A | | 8/2000 | Ullman et al. |
| 6,116,516 | A | | 9/2000 | Ganan-Calvo |
| 6,120,666 | A | | 9/2000 | Jacobson et al. |
| 6,124,439 | A | * | 9/2000 | Friedman et al. ....... 530/388.24 |
| 6,165,778 | A | | 12/2000 | Kedar |

(Continued)

FOREIGN PATENT DOCUMENTS

EP 1447127 B1 4/2007

(Continued)

OTHER PUBLICATIONS

Griffiths, The Embo Hournal, 22, 1, 24-35, 2003.*

(Continued)

*Primary Examiner*—Teresa D. Wessendorf
(74) *Attorney, Agent, or Firm*—Mintz, Levin, Cohn, Ferris, Glovsky and Popeo, P.C.; Ivor R. Elrifi; Matthew Pavao

(57) ABSTRACT

The invention describes a method for the synthesis of compounds comprising the steps of: (a) compartmentalizing two or more sets of primary compounds into microcapsules; such that a proportion of the microcapsules contains two or more compounds; and (b) forming secondary compounds in the microcapsules by chemical reactions between primary compounds from different sets. The invention further allows for the identification of compounds which bind to a target component of a biochemical system or modulate the activity of the target, and which is co-compartmentalized into the microcapsules.

8 Claims, 5 Drawing Sheets

U.S. PATENT DOCUMENTS

| | | | |
|---|---|---|---|
| 6,187,214 B1 | 2/2001 | Ganan-Calvo | |
| 6,248,378 B1 | 6/2001 | Ganan-Calvo | |
| 6,251,661 B1 | 6/2001 | Urabe et al. | |
| 6,268,222 B1 | 7/2001 | Chandler et al. | |
| 6,355,198 B1 | 3/2002 | Kim et al. | |
| 6,475,441 B1* | 11/2002 | Parce et al. | 422/100 |
| 6,489,103 B1* | 12/2002 | Griffiths et al. | 435/6 |
| 6,508,988 B1 | 1/2003 | Van Dam et al. | |
| 6,680,178 B2* | 1/2004 | Harris et al. | 435/23 |
| 6,766,817 B2 | 7/2004 | Da Silva | |
| 6,808,882 B2* | 10/2004 | Griffiths et al. | 435/6 |
| 6,918,404 B2 | 7/2005 | Dias da Silva | |
| 7,066,586 B2 | 6/2006 | Da Silva | |
| 7,138,233 B2 | 11/2006 | Griffiths et al. | |
| 7,541,383 B2* | 6/2009 | Fu et al. | 514/602 |
| 2001/0023078 A1 | 9/2001 | Bawendi et al. | |
| 2001/0041343 A1 | 11/2001 | Pankowsky | |
| 2001/0041344 A1 | 11/2001 | Sepetov et al. | |
| 2002/0005354 A1 | 1/2002 | Spence et al. | |
| 2002/0036139 A1 | 3/2002 | Becker et al. | |
| 2002/0164271 A1 | 11/2002 | Ho | |
| 2003/0148544 A1 | 8/2003 | Nie et al. | |
| 2004/0068019 A1 | 4/2004 | Higuchi et al. | |

FOREIGN PATENT DOCUMENTS

| | | |
|---|---|---|
| WO | WO 84/02000 | 5/1984 |
| WO | WO 96/29629 | 9/1996 |
| WO | WO 98/10267 | 3/1998 |
| WO | WO 99/02671 | 1/1999 |
| WO | WO 00/40712 | 7/2000 |
| WO | WO 01/14589 | 3/2001 |
| WO | WO 01/89787 | 11/2001 |
| WO | WO 02/22869 | 3/2002 |
| WO | WO 02/23163 | 3/2002 |
| WO | WO 02/31203 | 4/2002 |
| WO | WO 02/68104 | 6/2002 |
| WO | WO 02/103011 | 12/2002 |
| WO | WO 03/037302 | 5/2003 |
| WO | WO 03/078659 | 9/2003 |
| WO | WO 2004/002627 | 1/2004 |
| WO | WO 2004/024917 | 3/2004 |
| WO | WO 2004/088314 | 10/2004 |
| WO | WO 2004/091763 | 10/2004 |
| WO | WO 2005/021151 | 3/2005 |
| WO | WO 2006/038035 | 4/2006 |
| WO | WO 2006/040551 | 4/2006 |
| WO | WO 2006/040554 | 4/2006 |
| WO | WO 2006/096571 | 9/2006 |
| WO | WO 2007/089541 | 8/2007 |

OTHER PUBLICATIONS

Lim et al, Science, New Series, 210, 4472, 908-910.*
Adang et al., "The Contribution of Combinatorial Chemistry to Lead Generation: An Interim Analysis", Curr. Med. Chem., 8: 985-998, (2001).
Bernath et al., "In Vitro Compartmentalization by Double Emulsions: Sorting and Gene Enrichment by Fluorescence Activated Cell Sorting", Anal. Biochem., 325:151-157 (2004).
Burbaum, J.J., "Miniaturization Technologies in HTS: How Fast, How Small, How Soon? Drug Discovery", Drug Discovery Today, 3(7):313-322 (1998).
Curran, D.P., "Strategy-Level Separations in Organic Synthesis: From Planning to Practice", Angew. Chem. Int. Ed., 37:1174-1196 (1998).
Czarnik, A.W., "Encoding Methods for Combinatorial Chemistry", Curr. Opin. Chem. Biol., 1:60-66 (1997).
Davis et al., "Multiple Emulsions as Targetable Delivery Systems", Meth. Enzymol., 149: 51-64 (1987).
Dickinson, E., "Emulsions and Droplet Size Control", in Wedlock, D.J. (ed.), Controlled Particle, Droplet and Bubble Formulation, Butterworth-Heinemann, Oxford, Chapter 7, pp. 191-216 (1994).
Finch, C.A., "Industrial Microencapsulation: Polymers for Microcapsule Walls", Encapsulation and Controlled Release, Spec. Publ.-R. Soc. Chem., pp. 1-12 (1993).
Fu et al., "An Integrated Microfabricated Cell Sorter", Anal. Chem., 74:2451-2457 (2002).
Fulton. et al., "Advanced Multiplexed Analysis with the FlowMetrix™ System", Clin. Chem., 43:1749-1756 (1997).
Ghadessy et al, "Directed Evolution of Polymerase Function by Compartmentalized Self-Replication", Proc. Natl. Acad. Sci USA, 98(8):4552-4557 (2001).
Gordon et al., "Solid Phase Synthesis—Designer Linkers for Combinatorial Chemistry: A Review", J. Chem. Technol. Biotechnol, 74:835-851 (1999).
Griffiths et al., "Isolation of High Affinity Human Antibodies Directly from Large Synthetic Repertoires", EMBO. J., 13(14):3245-3260 (1994).
Griffiths et al., "Directed Evolution of an Extremely Fast Phosphotriesterase by In Vitro Compartmentalization", EMBO. J., 22(1):24-35 (2003).
Guixe et al., "Ligand-Induced Conformational Transitions in Escherichia coli Phosphofructokinase 2: Evidence for an Allosteric Site for MgATP$^{2-}$", Biochem., 37:13269-12375 (1998).
Han et al., "Quantum-dot-tagged Microbeads for Multiplexed Optical Coding of Biomolecules", Nat. Biotechnol., 19(7):631-635 (2001).
Handen, J. S., "High-Throughput Screening-Challenges for the Future", Drug Discov. World, pp. 47-50 (2002).
Heim et al., "Engineering Green Fluorescent Protein for Improved Brightness, Longer Wavelengths and Fluorescence Response Energy Transfer", Curr. Biol., 6(2):178-182 (1996).
Hergenrother et al., "Small-Molecule Microarrays: Covalent Attachment and Screening of Alcohol-Containing Small Molecules on Glass Slides", J. Am. Chem. Soc., 122:7849-7850 (2000).
Hildebrand et al., "Liquid-Liquid Solubility of Perfluoromethylcyclohexane with Benzene, Carbon Tetrachloride, Chlorobenzene, Chloroform and Toluene", J. Am. Chem. Soc., 71:22-25 (1949).
Holmes et al., "Reagents for Combinatorial Organic Synthesis: Development of a New O-Nitrobenzyl Photolabile Linder for Solid Phase Synthesis", J. Org Chem., 60:2318-2319 (1995).
Johannsson, A., "Heterogeneous Enzyme Immunoassays", In Principles and Practice of Immunoassay, pp. 295-325 (1991).
Johannsson et al., "Amplification by Second Enzymes", In ELISA and Other Solid Phase Immunoassays, Kemeny et al (ed.), Chapter 4, pp. 85-106 (1988).
Keij et al., "High-Speed Photodamage Cell Selection Using a Frequency-Doubled Argon Ion Laser", Cytometry, 19(3):209-216 (1995).
Kerker, M., "Elastic and Inelastic Light Scattering in Flow Cytometry $^{1,2}$", Cytometry, 4(1):1-10 (1983).
Krafft et al., "Emulsions and Microemulsions with a Fluorocarbon Phase", Curr. Op. Colloid Interface Sci., 8:251-258 (2003).
Link et al., "Geometrically Mediated Breakup of Drops in Microfluidic Devices", Phys. Rev. Lett., 92(5):054503-1 thru 054503-4 (2004).
Lipinski et al., "Experimental and Computational Approaches to Estimate Solubility and Permeability in Drug Discovery and Development Settings", Adv. Drug Deliv. Rev., 46:3-26 (2001).
Lowe, K. C., "Perfluorochemical Respiratory Gas Carriers: Benefits to Cell Culture Systems", J. Fluorine Chem., 118:19-26 (2002).
Luisi et al., "Activity and Conformation of Enzymes in Reverse Micellar Solutions", Meth. Enzymol., 136:188-216 (1987).
Lyne, P.D., "Structure-Based Virtual Screening: An Overview", Drug Discov. Today, 7(20):1047-1055 (2002).
Mackenzie et al., "The Application of Flow Microfluorimetry to Biomedical Research and Diagnosis: A Review", Dev. Biol. Stand., 64:181-193 (1986).
Mahajan et al., "Bc1-2 and Bax Interactions in Mitochondria Probed with Green Florescent Protein and Fluorescence Resonance Energy Transfer", Nat. Biotechnol. 16(6):547-552 (1998).

Masui et al., "Probing of DNA-Binding Sites of *Escherichia coli* RecA Protein Utilizing 1-anilinonaphthalene-8-Sulfonic Acid", *Biochem.*, 37(35):12133-12143 (1998).

Miyawaki et al., "Fluorescent Indicators for Ca2+ Based on Green Fluorescent Proteins and Calmodulin", *Nature*, 388:882-887 (1997).

Norman, A., "Flow Cytometry", *Med. Phys.*, 7(6):609-615 (1980).

Perelson, A.S., "Theoretical Studies of Clonal Selection: Minimal Antibody Repertoire Size and Reliability of Self-Non-Self Discrimination", *J. Theor. Biol.*, 81:645-670 (1979).

Pirrung et al., "A General Method for the Spatially Defined Immobilization of Biomolecules on Glass Surfaces Using 'Caged' Biotin", *Bioconjug. Chem.*, 7:317-321 (1996).

Qi et al., "Acid Beta-Glucosidase: Intrinsic Fluorescence and Conformational Changes Induced by Phospholipids and Saposin C", *Biochem.*, 37(33):11544-11554 (1998).

Ramstrom et al., "Drug Discovery by Dynamic Combinatorial Libraries", *Nat. Rev. Drug Discov.*, 1(1):26-36 (2002).

Riess, J.G., "Fluorous Micro- and Nanophases with a Biomedical Perspective", *Tetrahedron*, 58:4113-4131 (2002).

Rolland et al., "Review Article: Fluorescence Polarization Assay by Flow Cytometry", *J. Immunol. Meth.*, 76(1):1-10 (1985).

Sadtler et al., "Achieving Stable, Reverse Water-in-Fluorocarbon Emulsions", *Angew. Chem. Int. Ed. Engl.*, 35(17):1976-1978 (1996).

Scott, R. L., "The Solubility of Fluorocarbons", *J. Am. Chem. Soc.*, 70:4090-4093 (1948).

Sepp et al., "Microbead Display by In Vitro Compartmentalisation: Selection for Binding Using Flow Cytometry", *FEBS Lett.*, 532:455-458 (2002).

Song et al., "A Microfluidic System for Controlling Reaction Networks in Time", Angew. *Chem. Int. Ed. Engl.*, 42(7):767-772 (2003).

Studer et al., "Fluorous Synthesis: A Fluorous-Phase Strategy for Improving Separation Efficiency in Organic Synthesis", *Science* 275:823-826 (1997).

Sundberg et al., "Spatially-Addressable Immobilisation of Macromolecules on Solid Supports", *J. Am. Chem. Soc.*, 117:12050-12057 (1995).

Thorsen et al., "Dynamic Pattern Formation in a Vesticle-Generating Microfluidic Device", *Phys. Rev. Lett.*, 86(18):4163-4166 (2001).

Voss, E. W., "Kinetic Measurements of Molecular Interactions by Spectrofluorometry", *J. Mol. Recognition*, 6:51-58 (1993).

\* cited by examiner

METHOD OF SYNTHESIS AND TESTING OF COMBINATORIAL LIBRARIES USING MICROCAPSULES

RELATED APPLICATIONS

This application is a continuation which claims priority under 35 U.S.C. §120 to PCT Application No. PCT/GB2004/001352, filed Mar. 31, 2004, which claims priority under 35 U.S.C. §119 to Great Britain Application Serial No. 0307428.3, filed Mar. 31, 2003, the entireties of which are incorporated herein by reference.

The present invention relates to methods for use in the synthesis and identification of molecules which bind to a target component of a biochemical system or modulate the activity of a target.

Over the past decade, high-throughput screening (HTS) of compound libraries has become a cornerstone technology of pharmaceutical research. Investment into HTS is substantial. A current estimate is that biological screening and preclinical pharmacological testing alone account for ~14% of the total research and development (R&D) expenditures of the pharmaceutical industry (Handen, Summer 2002). HTS has seen significant improvements in recent years, driven by a need to reduce operating costs and increase the number of compounds and targets that can be screened. Conventional 96-well plates have now largely been replaced by 384-well, 1536-well and even 3456-well formats. This, combined with commercially available plate-handling robotics allows the screening of 100,000 assays per day, or more, and significantly cuts costs per assay due to the miniaturisation of the assays.

HTS is complemented by several other developments. Combinatorial chemistry is a potent technology for creating large numbers of structurally related compounds for HTS. Currently, combinatorial synthesis mostly involves spatially resolved parallel synthesis. The number of compounds that can be synthesised is limited to hundreds or thousands but the compounds can be synthesised on a scale of milligrams or tens of milligrams, enabling full characterisation and even purification. Larger libraries can be synthesised using split synthesis on beads to generate one-bead-one compound libraries. This method is much less widely adopted due to a series of limitations including: the need for solid phase synthesis; difficulties characterising the final products (due to the shear numbers and small scale); the small amounts of compound on a bead being only sufficient for one or a few assays; the difficulty in identifying the structure of a hit compound, which often relies on tagging or encoding methods and complicates both synthesis and analysis. Despite this split synthesis and single bead analysis still has promise. Recently there have been significant developments in miniaturised screening and single bead analysis. For example, printing techniques allow protein-binding assays to be performed on a slide containing 10,800 compound spots, each of 1 nl volume (Hergenrother et al., 2000). Combichem has so far, however, generated only a limited number of lead compounds. As of Apr. 2000, only 10 compounds with a combinatorial chemistry history had entered clinical development and all but three of these are (oligo)nucleotides or peptides (Adang and Hermkens, 2001). Indeed, despite enormous investments in both HTS and combinatorial chemistry during the past decade the number of new drugs introduced per year has remained constant at best.

Dynamic combinatorial chemistry (DCC) can also be used to create dynamic combinatorial libraries (DCLs) from a set of reversibly interchanging components, however the sizes of libraries created and screened to date are still fairly limited ($\leqq$40,000) (Ramstrom and Lehn, 2002).

Virtual screening (VS) (Lyne, 2002), in which large compound bases are searched using computational approaches to identify a subset of candidate molecules for testing may also be very useful when integrated with HTS. However, there are to date few studies that directly compare the performance of VS and HTS, and further validation is required.

Despite all these developments, current screening throughput is still far from adequate. Recent estimates of the number of individual genes in the human genome (~30,000) and the number of unique chemical structures theoretically attainable using existing chemistries suggests that an enormous number of assays would be required to completely map the structure-activity space for all potential therapeutic targets (Burbaum, 1998).

Hence, a method with the capability to both create and screen vast numbers ($\geqq 10^{10}$) of compounds quickly, using reaction volumes of only a few femtolitres, and at very low cost should be of enormous utility in the generation of novel drug leads.

SUMMARY OF THE INVENTION

The invention, in a first aspect, provides a method for preparing a repertoire of compounds comprising the steps of:

(a) compartmentalising two or more sets of primary compounds into microcapsules; such that a proportion of the microcapsules contains multiple copies of one or more compounds representative of each of said sets, and wherein said one or more compounds represents a subset of the set of primary compounds; and (b) forming secondary compounds in the microcapsules by chemical reactions between primary compounds from different sets.

A compound is "representative" of a set where is is member of said set; advantageously, therefore, each microcapsule contains compound(s) from each set. Although a microcapsule may contain more than one different compound from each set, it contains only a proportion of said set—i.e. a subset. The subset of a set advantageously represents no more that 10% of the members of the set; preferably, this figure is 9%, 8%, 7%, 6%, 5%, 4%, 3%, 2%, 1% or less.

Most advantageously a microcapsule contains only a single compound from each set of primary compounds.

The sets of primary compounds used in the method of the invention can consist of any number of different compounds. At least a first set comprises two or more compounds; but the other set may be a single compound. Preferably, if a first set is a single compound, at least one further set comprises a repertoire of compounds. The larger this repertoire, the greater the number of different secondary compounds that will be generated.

Preferably, at least one set of compounds comprises a repertoire of different compounds. At least one set, however, may consist of a single compound, such that secondary compounds are all constructed based on or containing the single compound used in one set. The greater the number of sets, and the greater the diversity of each set, the greater the final diversity of the secondary compounds generated.

Advantageously, in step (a) the number of different compounds per compartment will be equivalent to the the number of primary compounds forming the secondary compound in step (b).

In a second aspect, the invention provides a method for identifying primary compounds which react together to form secondary compounds capable of binding to or modulating the activity of a target, comprising the steps of:

(a) compartmentalising two or more sets of primary compounds into microcapsules; such that a proportion of the microcapsules contains two or more compounds;

(b) forming secondary compounds in the microcapsules by chemical reactions between primary compounds from different sets; and (c) identifying subsets of primary compounds which react to form secondary compounds which bind to or modulate the activity of the target.

In a third aspect, the invention provides a method for synthesising compounds with enhanced ability to bind to or modulate the activity of the target, comprising the steps of:

(a) compartmentalising into microcapsules subsets of primary compounds identified in step (c) of the second aspect of the invention and, optionally, compartmentalising additional sets of primary compounds;

(b) forming secondary compounds in the microcapsules by chemical reactions between primary compounds from different sets; and (c) identifying subsets of primary compounds which react to form secondary compounds which bind to or modulate the activity of the target.

Advantageously, steps (a) to (c) can be repeated, but after the first cycle, step (a) comprises compartmentalising subsets of primary compounds identified in step (c) into microcapsules and, optionally, compartmentalising additional sets of compounds.

In a fourth aspect, the invention provides a method for identifying individual compounds which bind to or modulate the activity of the target, comprising the steps of:

(a) compartmentalising into microcapsules a primary compound identified in step (c) of the second or third aspect of the invention and additional sets of primary compounds;

(b) forming secondary compounds in the microcapsules by chemical reactions between primary compounds from different sets; and (c) identifying subsets of primary compounds which react to form secondary compounds which bind to or modulate the activity of the target.

If the secondary compound is formed by the chemical reaction between more than two primary compounds it can be identified by iteratively repeating steps (a) to (c), but after the first cycle, step (c) comprises compartmentalising the primary compound identified in step (c) of the second or third aspect of the invention, a primary compound identified in step (c) of each of the previous cycles (of the fourth aspect of the invention) and additional sets of primary molecules.

Preferably, the desired activity is selected from the group consisting of a binding activity and the modulation of the activity of a target. Advantageously, the target is compartmentalised into microcapsules together with the compounds.

Sets of compounds may be compartmentalised in different ways to achieve encapsulation of multiple copies of two or more compounds into microcapsules.

For example, small aliquots of an aqueous solution of each compound can be deposited into an oil phase (advantageously containing surfactants and/or other stabilising molecules) whilst applying mechanical energy, thereby dispersing each compound into multiple aqueous microcapsules, each of which contains (for the most part) a single sort of compound but multiple copies thereof. Advantageously, the compounds can be deposited into the oil phase in the form of droplets generated using inkjet printing technology (Calvert, 2001; de Gans et al., 2004), and more advantageously by piezoelectric drop-on-demand (DOD) inkjet printing technology. Inkjet printing technology can be used to mix primary compounds and, optionally, other reagents (e.g the target and reagents to assay target activity) immediately prior to forming the emulsion. Advantageously, multiple compounds can be mixed with multiple targets in a combinatorial manner.

Thus, step (a) above can be modified such that it comprises forming separate emulsion compartments containing two or more compounds and mixing the emulsion compartments to form an emulsified compound repertoire wherein a subset of the repertoire is represented in multiple copies in any one microcapsule.

Moreover, compound libraries can be be compartmentalised in highly monodisperse microcapsules produced using microfluidic techniques. For example, aliquots of each compound can be compartmentalised into one or more aqueous microcapsules (with less than 3% polydispersity) in water-in-oil emulsions created by droplet break off in a co-flowing steam of oil (Umbanhowar et al., 2000). Advantageously, the aqueous microcapsules are then transported by laminar-flow in a stream of oil in microfluidic channels (Thorsen et al., 2001). The microcapsules containing single compounds can, optionally, be split into two or more smaller microcapsules using microfluidics (Link et al., 2004; Song et al., 2003). Microcapsules containing primary compounds can be fused with other microcapsules (Song et al., 2003) to form secondary compounds. Microcapsules containing compounds can also, optionally, be fused with microcapsules containing a target. A single microcapsule containing a target can, optionally, be split into two or more smaller microcapsules which can subsequently be fused with microcapsules containing different compounds, or compounds at different concentrations. Advantageously, a compound and a target can be mixed by microcapsule fusion prior to a second microcapsule fusion which delivers the reagents necessary to assay the activity of the target (e.g. the substrate for the target if the target is an enzyme). This allows time for the compound to bind to the target. The microcapsules can be analysed and, optionally, sorted using microfluidic devices (Fu et al., 2002).

In a further aspect, there is provided a method for preparing a repertoire of compounds comprising the steps of:

(a) attaching two or more sets of primary compounds onto microbeads;

(b) compartmentalising the microbeads into microcapsules such that a proportion of the microcapsules contains two or more microbeads;

(c) releasing at least one of the sets of primary compounds from the microbeads;

(d) forming secondary compounds in the microcapsules by chemical reactions between primary compounds from different sets.

Advantageously, the compounds are cleavable from the beads. Where more than two sets of compounds are used, all the sets with the exception of one are cleavable; preferably, they are all cleavable. The compounds may be attached to the microbeads by photochemically cleavable linkers.

In a still further aspect, the invention provides a method for identifying primary compounds which react together to form secondary compounds capable of binding to or modulating the activity of a target, comprising the steps of:

(a) attaching two or more sets of primary compounds onto microbeads;

(b) compartmentalising the microbeads into microcapsules together with the target such that many compartments contain two or more microbeads;

(c) releasing the primary compounds from the microbeads;

(d) forming secondary compounds in the microcapsules by chemical reactions between primary compounds from different sets; and (e) identifying subsets of primary compounds which react to form secondary compounds which bind to or modulate the activity of the target.

Advantageously, in step (b) the modal number of microbeads per compartment will be equivalent to the number of primary compounds forming the secondary compound in step (d).

In a further aspect, the invention provides a method for synthesising compounds with enhanced ability to bind to or modulate the activity of the target, comprising the steps of:

(a) attaching onto microbeads subsets of primary compounds identified in step (e) of the second aspect of the invention and, optionally, attaching additional sets of primary compounds;

(b) compartmentalising the microbeads into microcapsules together with the target such that many compartments contain two or more microbeads;

(c) releasing the primary compounds from the microbeads;

(d) forming secondary compounds in the microcapsules by chemical reactions between primary compounds from different sets: and (e) identifying subsets of primary compounds which react to form secondary compounds which bind to or modulate the activity of the target.

Advantageously, steps (a) to (e) can be repeated, but after the first cycle, step (a) comprises attaching onto microbeads subsets of primary compounds identified in step (e) and, optionally, attaching additional sets of compounds.

In a further aspect, the invention provides a method for identifying individual compounds which bind to or modulate the activity of the target, comprising the steps of:

(a) attaching onto microbeads a primary compound identified in step (e) of the second or third aspect of the invention and additional sets of primary compounds;

(b) compartmentalising the microbeads into microcapsules together with the target such that many compartments contain two or more microbeads;

(c) releasing the primary compounds from the microbeads;

(d) forming secondary compounds in the microcapsules by chemical reactions between primary compounds from different sets; and (e) identifying subsets of primary compounds which react to form secondary compounds which bind to or modulate the activity of the target;

If the secondary compound is formed by the chemical reaction between more than two primary compounds it can be identified by iteratively repeating steps (a) to (e), but after the first cycle, step (a) comprises attaching onto microbeads the primary compound identified in step (e) of the second or third aspect of the invention, a primary compound identified in step (e) of each of the previous cycles (of the fourth aspect of the invention) and additional sets of primary molecules.

Preferably, the desired activity is selected from the group consisting of a binding activity and the modulation of the activity of a target. Advantageously, the target is compartmentalised into microcapsules together with the microbeads.

According to a preferred implementation of the present invention, the compounds may be screened according to an activity of the compound or derivative thereof which makes the microcapsule detectable as a whole. Accordingly, the invention provides a method wherein a compound with the desired activity induces a change in the microcapsule, or a modification of one or more molecules within the microcapsule, which enables the microcapsule containing the compound and, optionally, the microbead carrying it to be identified. In this embodiment, therefore, the microcapsules are either: (a) physically sorted from each other according to the activity of the compound(s) contained therein, and the contents of the sorted microcapsules analysed to determine the identity of the compound(s) which they contain; or (b) analysed directly without sorting to determine the identity of the compound(s) which the microcapsules contain.

According to a preferred embodiment of the present invention, the screening of compounds may be performed by, for example:

(I) In a first embodiment, the microcapsules are screened according to an activity of the compound or derivative thereof which makes the microcapsule detectable as a whole. Accordingly, the invention provides a method wherein a compound with the desired activity induces a change in the microcapsule, or a modification of one or more molecules within the microcapsule, which enables the microcapsule containing the compound and the microbead carrying it to be identified. In this embodiment, therefore, the microcapsules are either: (a) physically sorted from each other according to the activity of the compound(s) contained therein, the contents of the sorted microcapsules optionally pooled into one or more common compartments, and the microcapsule contents analysed to determine the identity of the compound(s); or (b) analysed directly without sorting to determine the identity of the compound(s) which the microcapsules contained. Where the microcapsule contains microbeads, the microbeads can be analysed to determine the compounds with which they are coated.

(II) In a second embodiment, microbeads are analysed following pooling of the microcapsules into one or more common compartments. In this embodiment, a compound having the desired activity modifies the microbead which carried it (and which resides in the same microcapsule) in such a way as to make it identifiable in a subsequent step. The reactions are stopped and the microcapsules are then broken so that all the contents of the individual microcapsules are pooled. Modified microbeads are identified and either: (a) physically sorted from each other according to the activity of the compound(s) coated on the microbeads, and the sorted microbeads analysed to determine the identity of the compound(s) with which they are/were coated; or (b) analysed directly without sorting to determine the identity of the compound(s) with which the microbeads are/were coated. It is to be understood, of course, that modification of the microbead may be direct, in that it is caused by the direct action of the compound, or indirect, in which a series of reactions, one or more of which involve the compound having the desired activity, leads to modification of the microbead. Advantageously, the target is bound to the microbead and is a ligand and the compound within the microcapsule binds, directly or indirectly, to said ligand to enable the isolation of the microbead. In another configuration, a substrate for the target is and is bound to the microbead, and the activity of the compound within the microcapsule results, directly or indirectly, in the conversion of said substrate into a product which remains part of the microbead and enables its isolation. Alternatively, the activity of the compound may prevent or inhibit the conversion of said substrate into product. Moreover, the product of the activity of the compound within the microcapsule can result, directly or indirectly, in the generation of a product which is subsequently complexed with the microbead and enables its identification.

(III) In a third embodiment, the microbeads are analysed following pooling of the microcapsules into one or more common compartments. In this embodiment, a compound with a desired activity induces a change in the microcapsule containing the compound and the microbead which carries it. This change, when detected, triggers the modification of the microbead within the compartment. The reactions are stopped and the microcapsules are then broken so that all the contents of the individual microcapsules are pooled. Modified microbeads are identified and either: (a) physically sorted from each other according to the activity of the compound(s) coated on the microbeads, and the sorted microbeads analysed to determine the identity of the compound(s) with which they are/were coated; or (b) analysed directly without sorting to determine the identity of the compound(s) with which the microbeads are/were coated.

The microcapsules or microbeads may be modified by the action of the compound(s) such as to change their optical properties. For example, the modification of the microbead can enable it to be further modified outside the microcapsule so as to induce a change in its optical properties.

In another embodiment, the change in optical properties of the microcapsules or microbeads is due to binding of a compound with distinctive optical properties to the target.

Moreover, the change in optical properties of the microcapsules or microbeads can be due to binding of a target with distinctive optical properties by the compound.

The change in the optical properties of the microcapsule may be due to modulation of the activity of the target by the compound. The compound may activate or inhibit the activity of the target. For example, if the target is an enzyme, the substrate and the product of the reaction catalysed by the target can have different optical properties. Advantageously, the substrate and product have different fluorescence properties. In the case where the microcapsules contain microbeads, both the substrate and the product can have similar optical properties, but only the product of the reaction, and not the substrate, binds to, or reacts with, the microbead, thereby changing the optical properties of the microbead.

The change in optical properties of the microcapsules or microbeads can also be due to the different optical properties of the target and the product of the reaction being selected. Where both target and product have similar optical properties, only the product of the reaction being selected, and not the target, binds to, or reacts with, the microbead, thereby changing the optical properties of the microcapsules or microbeads.

In a further configuration, further reagents specifically bind to, or specifically react with, the product (and not the substrate) attached to or contained in the microcapsule or microbead thereby altering the optical properties of the microcapsule or microbead.

Advantageously, microcapsules or microbeads are modified directly or indirectly by the activity of the compound are further modified by Tyramide Signal Amplification (TSA™; NEN), resulting directly or indirectly in a change in the optical properties of said microcapsules or microbeads thereby enabling their separation.

It is to be understood that the detected change in the compartment may be caused by the direct action of the compound, or indirect action, in which a series of reactions, one or more of which involve the compound having the desired activity leads to the detected change.

Where the compounds are attached to beads, the density with which compounds are coated onto the microbeads, combined with the size of the microcapsule will determine the concentration of the compound in the microcapsule. High compound coating densities and small microcapsules will both give higher compound concentrations which may be advantageous for the selection of molecules with a low affinity for the target. Conversely, low compound coating densities and large microcapsules will both give lower compound concentrations which may be advantageous for the selection of molecules with a high affinity for the target.

Preferably, microencapsulation is achieved by forming an emulsion.

The microbead can be nonmagnetic, magnetic or paramagnetic.

Advantageously, the microcapsules or microbeads are analysed by detection of a change in their fluorescence. For example, microbeads can be analysed by flow cytometry and, optionally sorted using a fluorescence activated cell sorter (FACS). The different fluorescence properties of the target and the product can be due to fluorescence resonance energy transfer (FRET).

In a further embodiment, the internal environment of the microcapsules can be modified by the addition of one or more reagents to the continuous phase of the emulsion. This allows reagents to be diffused in to the microcapsules during the reaction, if necessary.

The invention moreover relates to a method according to the preceding aspects, further comprising the step of isolating the secondary compound produced by reaction of the primary compounds and optionally further comprising the step of manufacturing one or more secondary compounds.

The invention also provides for a product when identified according to the invention. As used in this context, a "product" may refer to any compound, selectable according to the invention.

Further embodiments of the invention are described in the detailed description below and in the accompanying claims.

DETAILED DESCRIPTION OF THE INVENTION

Definitions

Figure 1:
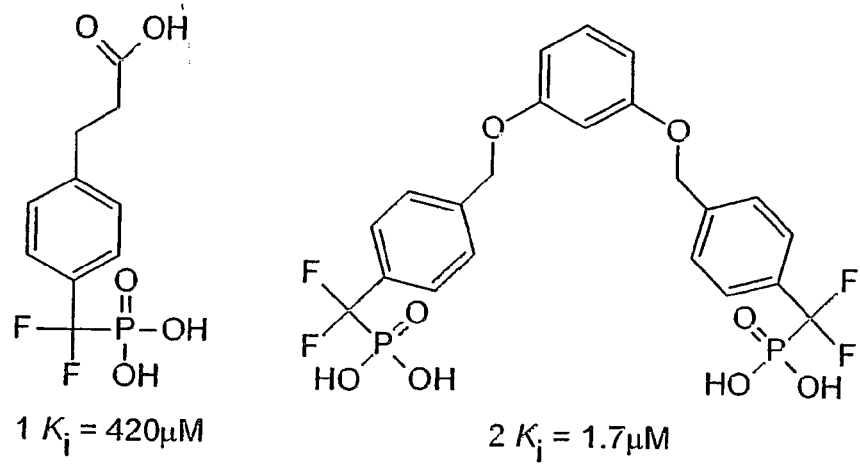
FIG. 1. Examples of PTP1B inhibitors. Compounds with a bis-difluoromethylene phosphonate moiety (e.g. 2) have significantly more potency than those with a single moiety (e.g. 1).

The term "microcapsule" is used herein in accordance with the meaning normally assigned thereto in the art and further described hereinbelow. In essence, however, a microcapsule is an artificial compartment whose delimiting borders restrict the exchange of the components of the molecular mechanisms described herein which allow the identification of the molecule with the desired activity. The delimiting borders preferably completely enclose the contents of the microcapsule. Preferably, the microcapsules used in the method of the present invention will be capable of being produced in very large numbers, and thereby to compartmentalise a library of compounds. Optionally, the compounds can be attached to microbeads. The microcapsules used herein allow mixing and sorting to be performed thereon, in order to facilitate the high throughput potential of the methods of the invention. Arrays of liquid droplets on solid surfaces, and multiwell plates, are not microcapsules as defined herein.

A "proportion" of the microcapsules, which is defined as comprising two or more compounds, or two or microbeads, is any fraction of the microcapsules in question, including all of said microcapsules. Advantageously, it is at least 25% thereof, preferably 50%, and more preferably 60%, 70%, 80% 90% or 95%.

The term "microbead" is used herein in accordance with the meaning normally assigned thereto in the art and further described hereinbelow. Microbeads, are also known by those skilled in the art as microspheres, latex particles, beads, or minibeads, are available in diameters from 20 nm to 1 nm and can be made from a variety of materials including silica and a variety of polymers, copolymers and terpolymers. Highly uniform derivatised and non-derivatised nonmagnetic and paramagnetic microparticles (beads) are commercially available from many sources (e.g. Sigma, Bangs Laboratories, Luminex and Molecular Probes) (Fornusek and Vetvicka, 1986).

Microbeads can be "compartmentalised" in accordance with the present invention by distribution into microcapsules. For example, in a preferred aspect the microbeads can be placed in a water/oil mixture and emulsified to form a water-in-oil emulsion comprising microcapsules according to the invention. The concentration of the microbeads can be adjusted to control the number of microbeads, which on average, appear in each microcapsule.

The term "compound" is used herein in accordance with the meaning normally assigned thereto in the art. The term compound is used in its broadest sense i.e. a substance comprising two or more elements in fixed proportions, including molecules and supramolecular complexes. This definition includes small molecules (typically <500 Daltons) which make up the majority of pharmaceuticals. However, the definition also includes larger molecules, including polymers, for example polypeptides, nucleic acids and carbohydrates, and supramolecular complexes thereof.

The term "primary compound" is used herein to indicate a compound which is compartmentalised in a microcapsule or coupled to a bead.

The term "secondary compound" is used herein to indicate a compound which is formed by the reaction between two or more primary compounds in a microcapsule, optionally after the release of at least one of the primary molecules from a microbead. Advantageously, all primary molecules are released from the microbeads. The secondary compound may be the result of a covalent or non-covalent reaction between the primary compounds.

The term "scaffold" is used herein in accordance with the meaning normally assigned thereto in the art. That is to say a core portion of a molecule common to all members of a combinatorial library (Maclean et al., 1999). Secondary compounds may optionally comprise scaffolds.

A "repertoire" of compounds is a group of diverse compounds, which may also be referred to as a library of compounds. Repertoires of compounds may be generated by any means known in the art, including combinatorial chemistry, compound evolution, or purchased from commercial sources such as Sigma Aldrich, Discovery Partners International, Maybridge and Tripos. A repertoire advantageously comprises at least $10^2, 10^3, 10^4, 10^5, 10^6, 10^7, 10^8, 10^9, 10^{10}, 10^{11}$ or more different compounds, which may be related or unrelated in structure or function.

A "set" of compounds may be a repertoire of compounds or any part of a repertoire, including a single compound species. The invention envisages the use of two or more sets of compounds, which are reacted together. The sets may be derived from a single repertoire, or a plurality of different repertoires.

Compounds can be "released" from a microbead by cleavage of a linker which effects the attachment of the compound to the microbead. Release of the compounds from the microbead allows the compounds to interact more freely with other contents of the microcapsule, and to be involved in reactions therein and optionally to become combined with other reagents to form new compounds, complexes, molecules or supramolecular complexes. Cleavage of linkers can be performed by any means, with means such as photochemical cleavage which can be effected from without the microcapsule being preferred. Photochemically cleavable linkers are known in the art (see for example (Gordon and Balasubramanian, 1999)) and further described below.

As used herein, the "target" is any compound, molecule, or supramolecular complex. Typical targets include targets of medical significance, including drug targets such as receptors, for example G protein coupled receptors and hormone receptors; transcription factors, protein kinases and phosphatases involved in signalling pathways; gene products specific to microorganisms, such as components of cell walls, replicases and other enzymes; industrially relevant targets, such as enzymes used in the food industry, reagents intended for research or production purposes, and the like.

An "activity", as referred to herein in connection with the modulation of an activity of a target, can be any activity of the target or an activity of a molecule which is influenced by the target, which is modulatable directly or indirectly by a compound or compounds as assayed herein. The activity of the target may be any measurable biological or chemical activity, including binding activity, an enzymatic activity, an activating or inhibitory activity on a third enzyme or other molecule, the ability to cause disease or influence metabolism or other functions, and the like. Activation and inhibition, as referred to herein, denote the increase or decrease of a desired activity 1.5 fold, 2 fold, 3 fold, 4 fold, 5 fold, 10 fold, 100 fold or more. Where the modulation is inactivation, the inactivation can be substantially complete inactivation. The desired activity may moreover be purely a binding activity, which may or may not involve the modulation of the activity of the target bound to.

A compound defined herein as "low molecular weight" or a "small molecule" is a molecule commonly referred to in the pharmaceutical arts as a "small molecule". Such compounds are smaller than polypeptides and other, large molecular complexes and can be easily administered to and assimilated by patients and other subjects. Small molecule drugs can advantageously be formulated for oral administration or intramuscular injection. For example, a small molecule may have a molecular weight of up to 2000 Dalton; preferably up to 1000 Dalton; advantageously between 250 and 750 Dalton; and more preferably less than 500 Dalton.

A "selectable change" is any change which can be measured and acted upon to identify or isolate the compound which causes it. The selection may take place at the level of the microcapsule, the microbead, or the compound itself, optionally when complexed with another reagent. A particularly advantageous embodiment is optical detection, in which the selectable change is a change in optical properties, which can 6e detected and acted upon for instance in a FACS device to separate microcapsules or microbeads displaying the desired change.

As used herein, a change in optical properties refers to any change in absorption or emission of electromagnetic radiation, including changes in absorbance, luminescence, phosphorescence or fluorescence. All such properties are included in the term "optical". Microcapsules or microbeads can be identified and, optionally, sorted, for example, by luminescence, fluorescence or phosphorescence activated sorting. In a preferred embodiment, flow cytometry is employed to identify and, optionally, sort microcapsules or microbeads. A variety of optical properties can be used for analysis and to trigger sorting, including light scattering (Kerker, 1983) and fluorescence polarisation (Rolland et al., 1985). In a highly preferred embodiment microcapsules or microbeads are analysed and, optionally, sorted using a fluorescence activated cell sorter (FACS) (Norman, 1980; Mackenzie and Pinder, 1986).

The compounds in microcapsules or on beads can be identified using a variety of techniques familiar to those skilled in the art, including mass spectroscopy, chemical tagging or optical tagging.

General Techniques

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference) and chemical methods. In addition Harlow & Lane, A Laboratory Manual Cold Spring Harbor, N.Y., is referred to for standard Immunological Techniques.

(A) General Description

The microcapsules of the present invention require appropriate physical properties to allow the working of the invention.

First, to ensure that the compounds and the target may not diff-use between microcapsules, the contents of each microcapsule must be isolated from the contents of the surrounding microcapsules, so that there is no or little exchange of compounds and target between the microcapsules over the timescale of the experiment.

Second, the method of the present invention requires that there are only a limited number of beads per microcapsule. This ensures that the compounds and the target will be isolated from other beads.

Third, the formation and the composition of the microcapsules must not abolish the activity of the target.

Consequently, any microencapsulation system used must fulfil these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase should be removed or the biological systems in it inhibited or destroyed in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an oil') as the matrix in which these droplets are suspended (the nondisperse, continuous or external phase). Such emulsions are termed water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and decane. Suitable surfactants include: non-ionic surfactants (Schick, 1966) such as sorbitan monooleate (Span™80; ICI), sorbitan monostearate (Span™60; ICI), polyoxyethylenesorbitan monooleate (Tween™ 80; ICI), and octylphenoxyethoxyethanol (Triton X-100); ionic surfactants such as sodium cholate and sodium taurocholate and sodium deoxycholate; chemically inert silicone-based surfactants such as polysiloxane-polycetyl-polyethylene glycol copolymer (Cetyl Dimethicone Copolyol) (e.g. Abil™EM90; Goldschmidt); and cholesterol.

Emulsions with a fluorocarbon (or perfluorocarbon) continuous phase (Krafft et al., 2003; Riess, 2002) may be particularly advantageous. For example, stable water-in-perfluorooctyl bromide and water-in-perfluorooctylethane emulsions can be formed using F-alkyl dimorpholinophosphates as surfactants (Sadtler et al., 1996). Non-fluorinated compounds are essentially insoluble in fluorocarbons and perfluorocarbons (Curran, 1998; Hildebrand and Cochran, 1949; Hudlicky, 1992; Scott, 1948; Studer et al., 1997) and small drug-like molecules (typically <500 Da and Log P<5) (Lipinski et al., 2001) are compartmentalised very effectively in the aqueous microcapsules of water-in-fluorocarbon and water-in-perfluorocarbon emulsions—with little or no exchange between microcapsules.

Advantageously, compounds can be compartmentalised in microcapsules comprising non-aqueous (organic) solvents. Non-fluorinated organic solvents are essentially insoluble and immiscible with fluorocarbons and perfluorocarbons (Curran, 1998; Hildebrand and Cochran, 1949; Hudlicky, 1992; Scott, 1948; Studer et al., 1997) allowing the formation of emulsions with a fluorocarbon (or perfluorocarbon) continuous phase and a discontinous phase formed from a non-aqueous solvent such as dichloromethane, chloroform, carbon tetrachloride, toluene, tetrahydrofuran, diethyl ether, and ethanol. The ability to form secondary compounds in microcapsules comprising non-aqueous solvents greatly expands the repertoire of chemical reactions that can be performed and secondary molecules that can be synthesised therein. Most of synthetic organic chemistry is carried out in organic solvents including dichloromethane, chloroform, carbon tetrachloride, toluene, tetrahydrofuran, diethyl ether, and ethanol. Organic molecules dissolve better in organic solvents. Electrostatic interactions are enhanced in organic solvents (due to the low dielectric constant), whereas they can be solvated and made less reactive in aqueous solvents. For example, much of contemporary organic chemistry involves reactions relating to carbonyl chemistry, including the use of metal enolates. Likewise for a growing number of other organometallic interactions. These reactions are often carried out under an inert atmosphere in anhydrous solvents (otherwise the reagents would be quenched by water). There are also a large number of reactions which use palladium catalysis including the Suzuki reaction and the Heck reaction.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Complicated biochemical processes, notably gene transcription and translation are also active in aqueous microcapsules formed in water-in-oil emulsions. This has enabled compartmentalisation in water-in-oil emulsions to be used for the selection of genes, which are transcribed and translated in emulsion microcapsules and selected by the binding or catalytic activities of the proteins they encode (Doi and Yanagawa, 1999; Griffiths and Tawfik, 2003; Lee et al., 2002; Sepp et al., 2002; Tawfik and Griffiths, 1998). This was possible because the aqueous microcapsules formed in the emulsion were generally stable with little if any exchange of nucleic acids, proteins, or the products of enzyme catalysed reactions between microcapsules.

The technology exists to create emulsions with volumes all the way up to industrial scales of thousands of litres (Becher, 1957; Sherman, 1968; Lissant, 1974; Lissant, 1984).

The preferred microcapsule size will vary depending upon the precise requirements of any individual screening process that is to be performed according to the present invention. In all cases, there will be an optimal balance between the size of the compound library and the sensitivities of the assays to determine the identity of the compound and target activity.

The size of emulsion microcapsules may be varied simply by tailoring the emulsion conditions used to form the emulsion according to requirements of the screening system. The larger the microcapsule size, the larger is the volume that will be required to encapsulate a given compound library, since the ultimately limiting factor will be the size of the microcapsule and thus the number of microcapsules possible per unit volume.

Water-in-oil emulsions can be re-emulsified to create water-in-oil-in water double emulsions with an external (continuous) aqueous phase. These double emulsions can be analysed and, optionally, sorted using a flow cytometer (Bernath et al., 2004).

Highly monodisperse microcapsules can be produced using microfluidic techniques. For example, water-in-oil emulsions with less than 3% polydispersity can be generated by droplet break off in a co-flowing steam of oil (Umbanhowar et al., 2000). Microfluidic systems can also be used for laminar-flow of aqueous microdroplets dispersed in a stream of oil in microfluidic channels (Thorsen et al., 2001). This allows the construction of microfluidic devices for flow analysis and, optionally, flow sorting of microdroplets (Fu et al., 2002).

Microcapsules can, advantageously, be fused or split. For example, aqueous microdroplets can be merged and split using microfluidics systems (Link et al., 2004; Song et al., 2003). Microcapsule fusion allows the mixing of reagents. Fusion, for example, of a microcapsule containing the target with a microcapsule containing the compound could initiate the reaction between target and compound. Microcapsule splitting allows single microcapsules to be split into two or more smaller microcapsules. For example a single microcapsule containing a compound can be split into multiple microcapsules which can then each be fused with a different microcapsule containing a different target. A single microcapsule containing a target can also be split into multiple microcapsules which can then each be fused with a different microcapsule containing a different compound, or compounds at different concentrations.

Microcapsules can be optically tagged by, for example, incorporating fluorochromes. In a preferred configuration, the microcapsules are optically tagged by incorporating quantum dots: quantum dots of 6 colours at 10 concentrations would allow the encoding of $10^6$ microcapsules (Han et al., 2001). Microcapsules flowing in an ordered sequence in a microfluidic channel can be encoded (wholly or partially) by their sequence in the stream of microcapsules (positional encoding).

Microbeads, also known by those skilled in the art as microspheres, latex particles, beads, or minibeads, are available in diameters from 20 nm to 1 mm and can be made from a variety of materials including silica and a variety of polymers, copolymers and terpolymers including polystyrene (PS), polymethylmethacrylate (PMMA), polyvinyltoluene (PVT), styrene/butadiene (S/B) copolymer, and styrene/vinyltoluene (S/VT) copolymer They are available with a variety of surface chemistries from hydrophobic surfaces (e.g. plain polystyrene), to very hydrophilic surfaces imparted by a wide variety of functional surface groups: aldehyde, aliphatic amine, amide, aromatic amine, carboxylic acid, chloromethyl, epoxy, hydrazide, hydroxyl, sulfonate and tosyl. The functional groups permit a wide range of covalent coupling reactions for stable or reversible attachment of compounds to the microbead surface.

Microbeads can be optically tagged by, for example, incorporating fluorochromes. For example, one hundres difference bead sets have been created, each with a unique spectral address due to labeling with precise rations of red (>650) and orange (585 nm) fluorochromes (Fulton et al., 1997) and sets of up to $10^6$ beads can be encoded by incorporating quantum dots of 10 intensities and 6 colours (Han et al., 2001)

The compounds can be connected to the microbeads either covalently or non-covalently by a variety of means that will be familiar to those skilled in the art (see, for example, (Hermanson, 1996)). Advantageously, the compounds are attached via a cleavable linker. A variety of such linkers are familiar to those skilled in the art (see for example (Gordon and Balasubramanian, 1999)), including for example, linkers which can be cleaved photochemically and reversible covalent bonds which can be controlled by changing the pH (e.g. imines and acylhydrazones), by adjusting the oxido-reductive properties (e.g. disulphides), or using an external catalyst (e.g. cross-metathesis and transamidation).

The method of the present invention permits the identification of compounds which modulate the activity of the target in a desired way in pools (libraries or repertoires) of compounds.

In a highly preferred application, the method of the present invention is useful for screening libraries of compounds. The invention accordingly provides a method according to preceding aspects of the invention, wherein the compounds are identified from a library of compounds.

The compounds identified according to the invention are advantageously of pharmacological or industrial interest, including activators or inhibitors of biological systems, such as cellular signal transduction mechanisms suitable for diagnostic and therapeutic applications. In a preferred aspect, therefore, the invention permits the identification of clinically or industrially useful products. In a further aspect of the invention, there is provided a product when isolated by the method of the invention.

The selection of suitable encapsulation conditions is desirable. Depending on the complexity and size of the compound library to be screened, it may be beneficial to set up the encapsulation procedure such that one or less than one secondary compound is formed per microcapsule. This will provide the greatest power of resolution. Where the library is larger and/or more complex, however, this may be impracticable; it may be preferable to form several secondary compounds together and rely on repeated application of the method of the invention to identify the desired compound. A combination of encapsulation procedures may be used to identify the desired compound.

Theoretical studies indicate that the larger the number of compounds created the more likely it is that a compound will be created with the properties desired (see (Perelson and Oster, 1979) for a description of how this applies to repertoires of antibodies). It has also been confirmed practically that larger phage-antibody repertoires do indeed give rise to more antibodies with better binding affinities than smaller repertoires (Griffiths et al., 1994). To ensure that rare variants are generated and thus are capable of being identified, a large library size is desirable. Thus, the use of optimally small microcapsules is beneficial.

The largest repertoires of compounds that can be screened in a single experiment to date, using two dimensional microarrays of 1 nl volume spots, is ~$10^3$ (Hergenrother et al., 2000). Using the present invention, at a microcapsule diameter of 2.6 mm (Tawfik and Griffiths, 1998), by forming a three-dimensional dispersion, a repertoire size of at least $10^{11}$ can be screened using 1 ml aqueous phase in a 20 ml emulsion.

In addition to the compounds, or microbeads coated with compounds, described above, the microcapsules according to the invention will comprise further components required for the screening process to take place. They will comprise the target and a suitable buffer. A suitable buffer will be one in which all of the desired components of the biological system are active and will therefore depend upon the requirements of each specific reaction system. Buffers suitable for biological and/or chemical reactions are known in the art and recipes provided in various laboratory texts, such as (Sambrook and Russell, 2001).

Other components of the system will comprise those necessary for assaying the activity of the target. These may for example comprise substrate(s) and cofactor(s) for a reaction catalysed by the target, and ligand(s) bound by the target. They may also comprise other catalysts (including enzymes), substrates and cofactors for reactions coupled to the activity of the target which allow for the activity of the target to be detected.

(B) Screening Procedures

To screen compounds which bind to or modulate the activity of a target, the target is compartmentalised in microcapsules together with one or more compounds or compound-coated microbeads. Advantageously each microcapsule contains only a single sort of secondary compound, but many copies thereof. Advantageously each microbead is coated with only a single sort of compound, but many copies thereof. Advantageously the compounds are connected to the microbeads via a cleavable linker, allowing them to be released from the microbeads in the compartments. Advantageously, each microcapsule or microbead is optically tagged to allow identification of the compounds contained within the microcapsule of attached to the microbead.

(i) Screening for Binding

Compounds can be screened directly for binding to a target. In this embodiment, if the compound is attached to a microbead and has affinity for the target it will be bound by the target. At the end of the reaction, all of the microcapsules are combined, and all microbeads pooled together in one environment. Microbeads carrying compounds exhibiting the desired binding can be selected by affinity purification using a molecule that specifically binds to, or reacts specifically with, the target.

In an alternative embodiment, the target can be attached to microbeads by a variety of means familiar to those skilled in the art (see for example (Hermanson, 1996)). The compounds to be screened contain a common feature—a tag. The compounds are released from the microbeads and if the compound has affinity for the target, it will bind to it. At the end of the reaction, all of the microcapsules are combined, and all microbeads pooled together in one environment. Microbeads carrying compounds exhibiting the desired binding can be selected by affinity purification using a molecule that specifically binds to, or reacts specifically with, the "tag".

In an alternative embodiment, microbeads may be screened on the basis that the compound, which binds to the target, merely hides the ligand from, for example, further binding partners. In this eventuality, the microbead, rather than being retained during an affinity purification step, may be selectively eluted whilst other microbeads are bound.

Sorting by affinity is dependent on the presence of two members of a binding pair in such conditions that binding may occur. Any binding pair may be used for this purpose. As used herein, the term binding pair refers to any pair of molecules capable of binding to one another. Examples of binding pairs that may be used in the present invention include an antigen and an antibody or fragment thereof capable of binding the antigen, the biotin-avidin/streptavidin pair (Savage et al., 1994), a calcium-dependent binding polypeptide and ligand thereof (e.g. calmodulin and a calmodulin-binding peptide (Montigiani et al., 1996; Stofko et al., 1992), pairs of polypeptides which assemble to form a leucine zipper (Tripet et al., 1996), histidines (typically hexahistidine peptides) and chelated $Cu^{2+}$, $Zn^{2+}$ and $Ni^{2+}$, (e.g. Ni-NTA; (Hochuli et al., 1987)), RNA-binding and DNA-binding proteins (Klug, 1995) including those containing zinc-finger motifs (Klug and Schwabe, 1995) and DNA methyltransferases (Anderson, 1993), and their nucleic acid binding sites.

In an alternative embodiment, compounds can be screened for binding to a target using a change in the optical properties of the microcapsule or the microbead.

The change in optical properties of the microcapsule or the microbead after binding of the compound to the target may be induced in a variety of ways, including:

(1) the compound itself may have distinctive optical properties, for example, it is fluorescent (2) the optical properties of the compound may be modified on binding to the target, for example, the fluorescence of the compound is quenched or enhanced on binding (Voss, 1993; Masui and Kuramitsu, 1998).

(3) the optical properties of the target may be modified on binding of the compound, for example, the fluorescence of the target is quenched or enhanced on binding (Guixe et al., 1998; Qi and Grabowski, 1998)

(4) the optical properties of both target and compound are modified on binding, for example, there can be a fluorescence resonance energy transfer (FRET) from target to compound (or vice versa) resulting in emission at the "acceptor" emission wavelength when excitation is at the "donor" absorption wavelength (Heim & Tsien, 1996; Mahajan et al., 1998; Miyawaki et al., 1997).

The invention provides a method wherein a compound with the desired activity induces a change in the optical properties of the microcapsule, which enables the microcapsule containing the compound and the microbeads contained therein to be identified, and optionally, sorted.

In an alternative embodiment, the invention provides a method wherein microbeads are analysed following pooling of the microcapsules into one or more common compartments. In this embodiment, a compound having the desired activity modifies the optical properties of the microbead which carried it (and which resides in the same microcapsule) to allow it to be identified, and optionally, sorted.

In this embodiment, it is not necessary for binding of the compound to the target to directly induce a change in optical properties.

In this embodiment, if the compound attached to the microbead has affinity for the target it will be bound by the target. At the end of the reaction, all of the microcapsules are combined, and all microbeads pooled together in one environment. Microbeads carrying compounds exhibiting the desired binding can be identified by adding reagents that specifically bind to, or react specifically with, the target and thereby induce a change in the optical properties of the microbeads allowing their identification. For example, a fluorescently-labelled anti-target antibody can be used, or an anti-target antibody followed by a second fluorescently labelled antibody which binds the first.

In an alternative embodiment, the target can be attached to the microbeads by a variety of means familiar to those skilled in the art (see for example (Hermanson, 1996)). The compounds to be screened contain a common feature—a tag. The compounds are released from the microbeads and if the compound has affinity for the target, it will bind to it. At the end of the reaction, all of the microcapsules are combined, and all microbeads pooled together in one environment. Microbeads carrying compounds exhibiting the desired binding can be identified by adding reagents that specifically bind to, or react specifically with, the "tag" and thereby induce a change in the optical properties of the microbeads allowing their identification. For example, a fluorescently-labelled anti-"tag" antibody can be used, or an anti-"tag" antibody followed by a second fluorescently labelled antibody which binds the first.

In an alternative embodiment, microbeads may be identified on the basis that the gene product, which binds to the ligand, merely hides the ligand from, for example, further binding partners which would otherwise modify the optical properties of the microbeads. In this case microbeads with unmodified optical properties would be selected.

Fluorescence may be enhanced by the use of Tyramide Signal Amplification (TSA™) amplification to make the microbeads fluorescent (Sepp et al., 2002). This involves peroxidase (linked to another compound) binding to the microbeads and catalysing the conversion of fluorescein-tyramine in to a free radical form which then reacts (locally) with the microbeads. Methods for performing TSA are known in the art, and kits are available commercially from NEN.

TSA may be configured such that it results in a direct increase in the fluorescence of the microbeads, or such that a ligand is attached to the microbeads which is bound by a second fluorescent molecule, or a sequence of molecules, one or more of which is fluorescent.

(ii) Screening for Regulation of Binding

In an alternative embodiment, the invention can be used to screen compounds which act to regulate a biochemical process. If the compound activates a binding activity of a target, a ligand for the target which is activated can be attached to microbeads by a variety of means familiar to those skilled in the art (see for example (Hermanson, 1996)). At the end of the reaction, all of the microcapsules are combined, and all microbeads pooled together in one environment. Microbeads carrying compounds exhibiting the desired binding can be selected by affinity purification using a molecule that specifically binds to, or reacts specifically with, the target.

In an alternative embodiment, microbeads may be screened on the basis that the compound inhibits the binding activity of a target. In this eventuality, the microbead, rather than being retained during an affinity purification step, may be selectively eluted whilst other microbeads are bound.

In an alternative embodiment, compounds can be screened for the ability to modulates a binding activity of a target using a change in the optical properties of the microcapsule or the microbead.

The change in optical properties of the microcapsule or the microbead after binding of the target to its ligand may be induced in a variety of ways, including:

(1) the ligand itself may have distinctive optical properties, for example, it is fluorescent
(2) the optical properties of the ligand may be modified on binding to the target, for example, the fluorescence of the ligand is quenched or enhanced on binding (Voss, 1993; Masui and Kuramitsu, 1998).
(3) the optical properties of the target may be modified on binding of the ligand, for example, the fluorescence of the target is quenched or enhanced on binding (Guixe et al., 1998; Qi and Grabowski, 1998)
(4) the optical properties of both target and ligand are modified on binding, for example, there can be a fluorescence resonance energy transfer (FRET) from target to ligand (or vice versa) resulting in emission at the "acceptor" emission wavelength when excitation is at the "donor" absorption wavelength (Heim & Tsien, 1996; Mahajan et al., 1998; Miyawaki et al., 1997).

The invention provides a method wherein a compound with the desired activity induces a change in the optical properties of the microcapsule, which enables the microcapsule containing the compound and the microbeads contained therein to be identified, and optionally, sorted.

In an alternative embodiment, the invention provides a method wherein microbeads are analysed following pooling of the microcapsules into one or more common compartments. In this embodiment, a compound having the desired activity modifies the optical properties of the microbead which carried it (and which resides in the same microcapsule) to allow it to be identified, and optionally, sorted.

In this embodiment, it is not necessary for binding of the target to the ligand to directly induce a change in optical properties.

In this embodiment, if a ligand attached to the microbead has affinity for the target it will be bound by the target. At the end of the reaction, all of the microcapsules are combined, and all microbeads pooled together in one environment. Microbeads carrying compounds which modulate the binding activity can be identified by adding reagents that specifically bind to, or react specifically with, the target and thereby induce a change in the optical properties of the microbeads allowing their identification. For example, a fluorescently-labelled anti-target antibody can be used, or an anti-target antibody followed by a second fluorescently labelled antibody which binds the first.

In an alternative embodiment, the target can be attached to the microbeads by a variety of means familiar to those skilled in the art (see for example (Hermanson, 1996)). The ligand to be screened contains a feature—a tag. At the end of the reaction, all of the microcapsules are combined, and all microbeads pooled together in one environment. Microbeads carrying compounds which modulate binding can be identified by adding reagents that specifically bind to, or react specifically with, the "tag" and thereby induce a change in the optical properties of the microbeads allowing their identification. For example, a fluorescently-labelled anti-"tag" antibody can be used, or an anti-"tag" antibody followed by a second fluorescently labelled antibody which binds the first.

Fluorescence may be enhanced by the use of Tyramide Signal Amplification (TSA™) amplification to make the microbeads fluorescent (Sepp et al., 2002), as above.

(iii) Screening for Regulation of Catalysis

In an alternative embodiment, the invention provides a method wherein a compound with the desired activity induces a change in the optical properties of the microcapsule, which enables the microcapsule containing the compound and, optionally, the microbeads contained therein to be identified, and optionally, sorted. The optical properties of microcapsules can be modified by either:

(a) the substrate and product of the regulated reaction having different optical properties (many fluorogenic enzyme substrates are available commercially, see for example (Haugland, 1996) including substrates for glycosidases, phosphatases, peptidases and proteases, or (b) the presence of reagents which specifically bind to, or react with, the product (or substrate) of the regulated reaction in the microcapsule and which thereby induce a change in the optical properties of the microcapsules allowing their identification.

A wide range of assays for screening libraries of compounds for those which modulate the activity of a target are based on detecting changes in optical properties and can be used to screen compounds according to this invention. Such assays are well known to those skilled in the art (see for example Haugland, 1996).

Alternatively, selection may be performed indirectly by coupling a first reaction to subsequent reactions that takes place in the same microcapsule. There are two general ways in which this may be performed. First, the product of the first reaction could be reacted with, or bound by, a molecule which does not react with the substrate(s) of the first reaction. A second, coupled reaction will only proceed in the presence of the product of the first reaction. A regulatory compound can then be identified by the properties of the product or substrate of the second reaction.

Alternatively, the product of the reaction being selected may be the substrate or cofactor for a second enzyme-catalysed reaction. The enzyme to catalyse the second reaction can be incorporated in the reaction mixture prior to microencapsulation. Only when the first reaction proceeds will the coupled enzyme generate an identifiable product.

This concept of coupling can be elaborated to incorporate multiple enzymes, each using as a substrate the product of the previous reaction. This allows for selection of regulators of enzymes that will not react with an immobilised substrate. It can also be designed to give increased sensitivity by signal amplification if a product of one reaction is a catalyst or a cofactor for a second reaction or series of reactions leading to a selectable product (for example, see (Johannsson, 1991; Johannsson and Bates, 1988). Furthermore an enzyme cascade system can be based on the production of an activator for an enzyme or the destruction of an enzyme inhibitor (see (Mize et al., 1989)). Coupling also has the advantage that a common screening system can be used for a whole group of enzymes which generate the same product and allows for the selection of regulation of complicated multi-step chemical transformations and pathways.

In an alternative embodiment, if the target is itself an enzyme, or regulates a biochemical process which is enzymatic, the microbead in each microcapsule may be coated with the substrate for the enzymatic reaction. The regulatory compound will determine the extent to which the substrate is converted into the product. At the end of the reaction the microbead is physically linked to the product of the catalysed reaction. When the microcapsules are combined and the reactants pooled, microbeads which were coated with activator compounds can be identified by any property specific to the product. If an inhibitor is desired, selection can be for a chemical property specific to the substrate of the regulated reaction.

It may also be desirable, in some cases, for the substrate not to be attached to the microbead. In this case the substrate would contain an inactive "tag" that requires a further step to activate it such as photoactivation (e.g. of a "caged" biotin analogue, (Pirrung and Huang, 1996; Sundberg et al., 1995)). After convertion of the substrate to product the "tag" is activated and the "tagged" substrate and/or product bound by a tag-binding molecule (e.g. avidin or streptavidin) attached to the microbead. The ratio of substrate to product attached to the nucleic acid via the "tag" will therefore reflect the ratio of the substrate and product in solution. A substrate tagged with caged biotin has been used to select for genes encoding enzymes with phosphotriesterase activity using a procedure based on compartmentalisation in microcapsules (Griffiths and Tawfik, 2003). The phosphotriesterase substrate was hydrolysed in solution in microcapsules containing active enzyme molecules, and after the reaction was completed, the caging group was released by irradiation to allow the product to bind, via the biotin moiety, to microbeads to which the gene encoding the enzyme was attached.

After the microbeads and the contents of the microcapsules are combined, those microbeads coated with regulators can be selected by affinity purification using a molecule (e.g. an antibody) that binds specifically to the product or substrate as appropriate.

In an alternative embodiment, the invention provides a method wherein the microbeads are analysed following pooling of the microcapsules into one or more common compartments. Microbeads coated with regulator compounds can be identified using changes in optical properties of the microbeads. The optical properties of microbeads with product (or substrate) attached can be modified by either:

(1) the product-microbead complex having characteristic optical properties not found in the substrate-microbead complex, due to, for example;

(a) the substrate and product having different optical properties (many fluorogenic enzyme substrates are available commercially (see for example Haugland, 1996) including substrates for glycosidases, phosphatases, peptidases and proteases, or (b) the substrate and product having similar optical properties, but only the product, and not the substrate binds to, or reacts with, the microbead;

(2) adding reagents which specifically bind to, or react with, the product (or substrate) and which thereby induce a change in the optical properties of the microbeads allowing their identification (these reagents can be added before or after breaking the microcapsules and pooling the microbeads). The reagents;

(a) bind specifically to, or react specifically with, the product, and not the substrate, (or vice versa) if both substrate and product are attached to the microbeads, or (b) optionally bind both substrate and product if only the product, and not the substrate binds to, or reacts with, the microbeads (or vice versa).

In this scenario, the substrate (or one of the substrates) can be present in each microcapsule unlinked to the microbead, but has a molecular "tag" (for example biotin, DIG or DNP or a fluorescent group). When the regulated enzyme converts the substrate to product, the product retains the "tag" and is then captured in the microcapsule by the product-specific antibody. When all reactions are stopped and the microcapsules are combined, these microbeads will be "tagged" and may already have changed optical properties, for example, if the "tag" was a fluorescent group. Alternatively, a change in optical properties of "tagged" microbeads can be induced by adding a fluorescently labelled ligand which binds the "tag" (for example fluorescently-labelled avidin/streptavidin, an anti-"tag" antibody which is fluorescent, or a non-fluorescent anti-"tag" antibody which can be detected by a second fluorescently-labelled antibody).

(iv) Screening for Compound Specificity/Selectivity

Compounds with specificity or selectivity for certain targets and not others can be specifically identified by carrying out a positive screen for regulation of a reaction using one substrate and a negative screen for regulation of a reaction with another substrate. For example, two substrates, specific for two different target enzymes, are each labelled with different fluorogenic moieties. Each target enzymes catalyse the generation of a product with with a different fluorescence spectrum resulting in different optical properties of the microcapsules depending on the specificity of the compound for two targets.

(v) Screening Using Cells

In the current drug discovery paradigm, validated recombinant targets form the basis of in vitro high-throughput screening (HTS) assays. Isolated proteins cannot, however, be regarded as representative of complex biological systems; hence, cell-based systems can provide greater confidence in compound activity in an intact biological system. A wide range of cell-based assays for drug leads are known to those skilled in the art. Cells can be compartmentalised in microcapsules, such as the aqeous microdroplets of a water-in-oil emulsion (Ghadessy, 2001). The effect of a compound(s) on a target can be determined by compartmentalising a cell (or cells) in a microcapsule together with a compound(s) and using an appropriate cell-based assay to identify those compartments containing compounds with the desired effect on the cell(s). The use of water-in-fluorocarbon emulsions may be particularly advantageous: the high gas dissolving capacity of fluorocarbons can support the exchange of respiratory gases and has been reported to be beneficial to cell culture systems (Lowe, 2002).

(vi) Flow Cytometry

In a preferred embodiment of the invention the microcapsules or microbeads will be analysed and, optionally, sorted by flow cytometry. Many formats of microcapsule can be analysed and, optionally, sorted directly using flow cytometry. Some formats of microcapsule may require that the microcapsules be further processed before analysis or sorting. For example, water-in-oil emulsions can be converted into water-in-oil-in-water double emulsions to facilitate analysis by flow cytometry (Bernath et al., 2004). Multiple emulsions are prepared by the re-emulsification of a simple primary water-in-oil (or oil-in-water) emulsion to provide water-in-oil-in-water (or oil-in-water-in-oil) emulsions (Davis and Walker, 1987).

Highly monodisperse microcapsules can be produced using microfluidic techniques. For example, water-in-oil emulsions with less than 3% polydispersity can be generated by droplet break off in a co-flowing steam of oil (Umbanhowar, 2000). Microfluidic systems can also be used for laminar-flow of aqueous microdroplets dispersed in a stream of oil in microfluidic channels (Thorsen, 2001). This allows the construction of microfluidic devices for flow analysis and, optionally, flow sorting of microdroplets (Fu, 2002).

A variety of optical properties can be used for analysis and to trigger sorting, including light scattering (Kerker, 1983) and fluorescence polarisation (Rolland et al., 1985). In a highly preferred embodiment the difference in optical properties of the microcapsules or microbeads will be a difference in fluorescence and, if required, the microcapsules or microbeads will be sorted using a fluorescence activated cell sorter (Norman, 1980; Mackenzie and Pinder, 1986), or similar device. Flow cytometry has a series of advantages:

(1) commercially available fluorescence activated cell sorting equipment from established manufacturers (e.g. Becton-Dickinson, Coulter, Cytomation) allows the analysis and sorting at up to 100,000 microcapsules or microbeads $s^{-1}$.

(2) the fluorescence signal from each microcapsule or microbead corresponds tightly to the number of fluorescent molecules present. As little as few hundred fluorescent molecules per microcapsules or microbeads can be quantitatively detected;

(3) the wide dynamic range of the fluorescence detectors (typically 4 log units) allows easy setting of the stringency of the sorting procedure, thus allowing the recovery of the optimal number microcapsules or microbeads from the starting pool (the gates can be set to separate microcapsules or microbeads with small differences in fluorescence or to only separate out microcapsules or microbeads with large differences in fluorescence, dependant on the selection being performed);

(4) commercially available fluorescence-activated cell sorting equipment can perform simultaneous excitation and detection at multiple wavelengths (Shapiro, 1995). allowing positive and negative selections to be performed simultaneously by monitoring the labelling of the microcapsules or microbeads with two to thirteen (or more) fluorescent markers, for example, if substrates for two alternative targets are labelled with different fluorescent tags the microcapsules or microbeads can labelled with different fluorophores dependent on the target regulated.

If the microcapsules or microbeads are optically tagged, flow cytometry can also be used to identify the compound or compounds in the microcapsule or coated on the microbeads (see below). Optical tagging can also be used to identify the concentration of the compound in the microcapsule (if more than one concentration is used in a single experiment) or the number of compound molecules coated on a microbead (if more than one coating density is used in a single experiment). Furthermore, optical tagging can be used to identify the target in a microcapsule (if more than one target is used in a single experiment). This analysis can be performed simultaneously with measuring activity, after sorting of microcapsules containing microbeads, or after sorting of the microbeads.

(vii) Microcapsule Identification and Sorting

The invention provides for the identification and, optionally, the sorting of intact microcapsules where this is enabled by the sorting techniques being employed. Microcapsules may be identified and, optionally, sorted as such when the change induced by the desired compound either occurs or manifests itself at the surface of the microcapsule or is detectable from outside the microcapsule. The change may be caused by the direct action of the compound, or indirect, in which a series of reactions, one or more of which involve the compound having the desired activity leads to the change. For example, where the microcapsule is a membranous microcapsule, the microcapsule may be so configured that a component or components of the biochemical system comprising the target are displayed at its surface and thus accessible to reagents which can detect changes in the biochemical system regulated by the compound on the microbead within the microcapsule.

In a preferred aspect of the invention, however, microcapsule identification and, optionally, sorting relies on a change in the optical properties of the microcapsule, for example absorption or emission characteristics thereof, for example alteration in the optical properties of the microcapsule resulting from a reaction leading to changes in absorbance, luminescence, phosphorescence or fluorescence associated with the microcapsule. All such properties are included in the term "optical". In such a case, microcapsules can be identified and, optionally, sorted by luminescence, fluorescence or phosphorescence activated sorting. In a highly preferred embodiment, flow cytometry is employed to analyse and, optionally, sort microcapsules containing compounds having a desired activity which result in the production of a fluorescent molecule in the microcapsule.

In an alternative embodiment, a change in microcapsule fluorescence, when identified, is used to trigger the modification of the microbead within the compartment. In a preferred aspect of the invention, microcapsule identification relies on a change in the optical properties of the microcapsule resulting from a reaction leading to luminescence, phosphorescence or fluorescence within the microcapsule. Modification of the microbead within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the microbead or molecules attached to it. A similar procedure has been described previously for the rapid sorting of cells (Keij et al., 1994). Modification of the microbead may result, for example, from coupling a molecular "tag", caged by a photolabile protecting group to the microbeads: bombardment with photons of an appropriate wavelength leads to the removal of the cage. Afterwards, all microcapsules are combined and the microbeads pooled together in one environment. Microbeads coated with compounds exhibiting the desired activity can be selected by affinity purification using a molecule that specifically binds to, or reacts specifically with, the "tag".

(C) Compound Libraries (i) Primary Compound Libraries

Libraries of primary compounds can be obtained from a variety of commercial sources. The compounds in the library can be made by a variety of means well known to those skilled in the art. Optionally, compound libraries can be made by combinatorial synthesis using spatially resolved parallel synthesis or using split synthesis, optionally to generate one-bead-one-compound libraries. The compounds can, optionally, be synthesised on beads. These beads can be compartmentalised in microcapsules directly or the compounds released before compartmentalisation.

Advantageously, only a single type of compound, but multiple copies thereof is present in each microcapsule.

The compounds can, optionally, be connected to microbeads either covalently or non-covalently by a variety of means that will be familiar to those skilled in the art (see, for example, (Hermanson, 1996)).

Microbeads are available with a variety of surface chemistries from hydrophobic surfaces (e.g. plain polystyrene), to very hydrophilic surfaces imparted by a wide variety of functional surface groups: aldehyde, aliphatic amine, amide, aromatic amine, carboxylic acid, chloromethyl, epoxy, hydrazide, hydroxyl, sulfonate and tosyl. The functional groups permit a wide range of covalent coupling reactions, well known to those skilled in the art, for stable or reversible attachment of compounds to the microbead surface.

Advantageously, the compounds are attached to the microbeads via a cleavable linker. A variety of such linkers are familiar to those skilled in the art (see for example (Gordon and Balasubramanian, 1999)), including for example, linkers which can be cleaved photochemically and reversible covalent bonds which can be controlled by changing the pH (e.g. imines and acylhydrazones), by adjusting the oxido-reductive properties (e.g. disulphides), or using an external catalyst (e.g. cross-metathesis and transamidation).

Advantageously, only a single type of compound, but multiple copies thereof is attached to each bead.

(ii) Secondary Compound Libraries

Secondary compound libraries are created by reactions between primary compounds in microcapsules. Secondary compounds can be created by a variety of two component, and multi-component reactions well known to those skilled in the art (Armstrong et al., 1996; Domling, 2002; Domling and Ugi, 2000; Ramstrom and Lehn, 2002).

To form secondary compound libraries by a two-component reaction, two sets of compounds are compartmentalised in microcapsules such that many compartments contain two or more compounds. Advantageously, the modal number of compounds per microcapsule is two. Advantageously, the microcapsules contain at least one type of compound from each set of compounds. Advantageously, the microcapsules contain one type of compound from each set of compounds. The secondary compounds are formed by chemical reactions between primary compounds from different sets. The secondary compound may be the result of a covalent or non-covalent reaction between the primary compounds.

A variety of chemistries, familiar to those skilled in the art, are suitable to form secondary compounds in two-component reactions. For example, reversible covalent bonds which can be controlled by changing the pH (e.g. imines and acylhydrazones), by adjusting the oxido-reductive properties (e.g. disulphides), or using an external catalyst (e.g. cross-metathesis and transamidation), can be used (Ramstrom and Lehn, 2002).

In a further embodiment, the method can also be used to create secondary compound libraries using three-component, four-component and higher order multi-component reactions. Three, four or more sets of compounds (as appropriate) are compartmentalised in microcapsules. The compounds are compartmentalised in microcapsules such that many compartments contain multiple compounds. Advantageously, the modal number of compounds per microcapsule is equal to the number of components in the reaction. Advantageously, the microcapsules contain at least one type of compound from each set of compounds. Advantageously, the microcapsules contain one type of compound from each set of compounds. The secondary compounds are formed by chemical reactions between primary compounds from different sets. The secondary compound may be the result of covalent or non-covalent reactions between the primary compounds.

Examples of suitable multi-component reactions are the Strecker, Hantzsch, Biginelli, Mannich, Passerini, Bucherer-Bergs and Pauson-Khand three-component reactions and the Ugi four-component reaction (Armstrong et al., 1996; Domling, 2002; Domling and Ugi, 2000).

Secondary compound libraries may also be built using a scaffold molecule which is common to all the secondary compounds (Ramstrom and Lehn, 2002). This scaffold molecule may be compartmentalised into microcapsules together with the other primary compounds.

In a further embodiment, to form secondary compound libraries by a two-component reaction, two sets of compounds are attached to microbeads, advantageously to give only a single type of molecule per microbead. The microbeads are compartmentalised in microcapsules such that many compartments contain two or more microbeads. Advantageously, the modal number of beads per microcapsule is two. The compounds comprising at least one of the two sets are released from the microbeads. The secondary compounds are formed by chemical reactions between primary compounds from different sets. The secondary compound may be the result of a covalent or non-covalent reaction between the primary compounds.

In a further embodiment, the method can also be used to create secondary compound libraries using three-component, four-component and higher order multi-component reactions. Three, four or more sets of compounds (as appropriate) are attached to microbeads, advantageously to give only a single type of molecule per microbead. The microbeads are compartmentalised in microcapsules such that many compartments contain multiple microbeads. Advantageously, the modal number of beads per microcapsule is equal to the number of components in the reaction. The compounds comprising either all, or all bar one, of the sets are released from the microbeads. The secondary compounds are formed by chemical reactions between primary compounds from different sets. The secondary compound may be the result of covalent or non-covalent reactions between the primary compounds.

Advantageously, the same reversible covalent bond can used to couple the primary compound to the microbead as is used to form the secondary compound.

Secondary compound libraries may also be built using a scaffold molecule which is common to all the secondary compounds (Ramstrom and Lehn, 2002). This scaffold molecule may be compartmentalised into microcapsules together with the microbeads.

(D) Identification of Compounds

The compounds in microcapsules or on microbeads can be identified in a variety of ways. If the identified microcapsules are sorted (e.g. by using a fluorescence activated cell sorter—FACS) the compounds can be identified by by direct analysis, for example by mass-spectroscopy. If the compounds remain attached to beads isolated as a result of selection (for example by affinity purification) or sorting (for example using a FACS) they can also be identified by direct analysis, for example by mass-spectroscopy. The microcapsules or beads can also be tagged by a variety of means well known to those skilled in the art and the tag used to identify the compound attached to the beads (Czarnik, 1997). Chemical, spectrometric, electronic, and physical methods to encode the compounds may all be used. In a preferred embodiment microcapsules or beads have different optical properties and are thereby optically encoded. In a preferred embodiment encoding is based on microcapsules or beads having different fluorescence properties. In a highly preferred embodiment the microcapsules or beads are encoded using fluorescent quantum dots present at different concentrations in the microcapsule or bead (Han, 2001). Microcapsules flowing in an ordered sequence in a microfluidic channel can also be encoded (wholly or partially) by their sequence in the stream of microcapsules (positional encoding).

Advantageously, each compounds is present in different microcapsules at different concentrations (typically at concentrations varying from mM to nM) allowing the generation of a dose-response curve. This would, for example, allow the determination of the inhibition constant ($K_i$) of an inhibitory compound. The concentration of the compounds in the microcapsules can be determined by, for example, optical encoding or positional encoding of the microcapsules or microbeads as above.

(E) Identification of Targets

Advantageously, multiple different targets can be compartmentalised in microcapsules such that each microcapsule contains multiple copies of the same target. For example, multiple protein kinases, or multiple polymorphic variants of a single target, can be compartmentalised to allow the specificity of compounds to be determined. The identity of the target in a microcapsule can be determined by, for example, optical encoding or positional encoding of the microcapsules or microbeads as above.

Expressed in an alternative manner, there is provided a method for the synthesis and identification of compounds which bind to a target component of a biochemical system or modulate the activity of the target, comprising the steps of:
  (a) compartmentalising two or more sets of primary compounds into microcapsules together with the target such that many compartments contain two or more primary compounds;
  (b) forming secondary compounds in the microcapsules by chemical reactions between primary compounds from different sets; and
  (c) identifying subsets of primary compounds which react to form secondary compounds which bind to or modulate the activity of the target.

There is also provided a method for the synthesis and identification of compounds which bind to a target component of a biochemical system or modulate the activity of the target, comprising the steps of:
  (1) attaching two or more sets of primary compounds onto microbeads;
  (2) compartmentalising the microbeads into microcapsules together with the target such that many compartments contain two or more microbeads;
  (3) releasing the primary compounds from the microbeads;
  (4) forming secondary compounds in the microcapsules by chemical reactions between primary compounds from different sets; and
  (5) identifying subsets of primary compounds which react to form secondary compounds which bind to or modulate the activity of the target.

If the primary compounds react, not only with other primary compounds in the same compartment, but also with other microbeads in the compartment, the primary compounds which react together to form a secondary compound can be identified by direct analysis of the compounds present on a microbeads isolated as a result of selection or sorting. For example, if the primary compounds are linked to the beads via a disulphide bond when they are released in the compartment the primary compounds will react both with each other to form a secondary compound and with the sulphydryl groups on the beads. Hence, if two beads are co-compartmentalised, each bead will end up carrying both primary compounds. After isolation of these beads both primary compounds which reacted to form the secondary compound can be identified.

Various aspects and embodiments of the present invention are illustrated in the following examples. It will be appreciated that modification of detail may be made without departing from the scope of the invention.

EXAMPLES

Example 1

Screening for Inhibitors of the Enzyme Protein Tyrosine Phosphatase 1B (PTP1B)

PTP1B is a negative regulator of insulin and leptin signal transduction. Resistance to insulin and leptin are hallmarks of type 2 diabetes mellitus and obesity and hence PTP1B is an attractive drug target for diabetes and obesity therapy (Johnson et al., 2002). Two water-in-oil emulsions are made as follows.

A solution of 1% (w/v) Span 60 and 1% (w/v) cholesterol in decane (all from Sigma Aldrich) is prepared by dissolving 80 mg of Span 60 and 80 mg of cholesterol into 7.84 ml of decane. The decane is heated to 45° C. to allow complete solubilization of the surfactant and cholesterol. The surfactant/decane solution is divided over batches of 200 µl and placed in a block-heater at 37° C.

A hand-extruding device (Mini extruder, Avanti Polar Lipids Inc, Alabaster, Ala., USA) is assembled according to the manufacturer's instructions. For extrusion, a single 19 mm Track-Etch polycarbonate filter with average pore size of 14 µm (Whatman Nuclepore, Whatman, Maidstone, UK) is fitted inside the mini extruder. Two gas-tight 1 ml Hamilton syringes (Gastight #1001, Hamilton Co, Reno, Nev., USA) are used for extrusion. The extruder was pre-rinsed with 3×1 ml of decane by loading one of the Hamilton syringes with 1 ml of decane, placing the syringe at one and of the mini extruder and extruding it through the filters into the empty Hamilton syringe on the other side of the extruder.

The first emulsion is made by loading 50 µl of 100 µM compound 2 (FIG. 1), which has a bis-difluoromethylene phosphonate and is a known PTP1B inhibitor (Johnson et al., 2002), the target enzyme (human recombinant PTP1B, residues 1-322; Biomol Research Laboratories, Inc.) at 5 mU/ml, the fluorogenic PTP1B substrate 6,8-difluoro-4-methylumbelliferyl phosphate (DiFMUP) (Molecular Probes), and 100 µM Texas Red (Sigma; excitation/emmission maxima 595/615 nm; red fluorescence) in a buffer compatible with PTP1B activity (25 mM HEPES, pH 7.4, 125 mM NaCl, 10% glycerol, 1 mM EDTA) (Doman et al., 2002) into one of the Hamilton syringes, and 200 µl of the pre-heated decane/surfactant mix into the other Hamilton syringe. The syringes are fitted into the openings on both sides of the filter holder of the extruder. The compound mix is forced through the filter holder into the alternate syringe containing the decane/surfactant mix and directly forced back into the original syringe to complete one round of extrusion. In total, 7.5 rounds of extrusion are completed. The filled syringe is removed from the extruder and emptied into a 1.7 ml Axygen tube (# MCT-175-C, Axygen Scientific, Inc., Union City, Calif., USA).

A second water-in-oil emulsion is made identical to the emulsion above but containing 100 µM hydrocinnamic acid (Aldrich), a compound that is not a PTP1B inhibitor, in place of compound 2, and 100 µM calcein (Sigma; excitation/emmission maxima 470/509 nm; green fluorescence) in place of Texas Red.

The two emulsions are mixed by vortexing in ratios varying from 1:1000 to 1:1 (compound 2 emulsion: hydrocinnamic acid emulsion) and incubated at 37° C. for 30 min. Inhibitors reduce the amount of non-fluorescent substrate (DiFMUP) converted to the dephosphorylated product (DiFMU; excitation/emmission maxima 358/452 nm; blue fluorescence).

The water-in-oil emulsions are then converted into water-in-oil-in water double emulsions as follows. The extruder (see above) is disassembled, cleaned extensively with soap and reversed-osmosis water, and re-assembled. A single 19 mm Track-Etch polycarbonate filter with an average pore size of 8 µm is fitted. The extruder is pre-rinsed with 3×1 ml phosphate-buffered saline solution (PBS). 750 µl of PBS containing 0.5% (w/v) Tween 80 (Sigma Aldrich) is loaded into a 1 ml gas-tight Hamilton syringe and fitted into the extruder. 250 µl of the water-in-oil emulsion is loaded into the alternate 1 ml Hamilton syringe and fitted into the extruder. The emulsion is forced through the filter into the alternate syringe containing the PBS/0.5% Tween 80 and immediately forced back into the original syringe to complete one cycle of extrusion. In total, 4.5 cycles of extrusion are performed. The filled syringe is removed from the extruder and emptied into a 1.7 ml Axygen tube. The water-in-oil-in-water double emulsions formed are placed on ice.

The double emulsions are then analysed by multi-colour flow cytometery using a MoFlo (Cytomation) flow cytometer. Predominantly, microcapsules exhibiting green fluorescence (and containing hydrocinnamic acid) also show blue fluorescence due to dephosphorylation of DiFMUP by PTP1B. Predominantly, microcapsules exhibiting red fluorescence (and containing containing compound 2) also show little or no blue fluorescence due to inhibition of PTP1B.

Example 2

Two aqueous mixtures are made on ice (to prevent reaction). The first mixture contains 100 µM compound 2 (FIG. 1), which has a bis-difluoromethylene phosphonate and is a known PTP1B inhibitor (Johnson et al., 2002), the target enzyme (human recombinant PTP1B, residues 1-322; Biomol Research Laboratories, Inc.) at 5 mU/ml, the fluorogenic PTP1B substrate 6,8-difluoro-4-methylumbelliferyl phosphate (DiFMUP) (Molecular Probes), and 100 µM Texas Red (Sigma; excitation/emmission maxima 595/615 nm; red fluorescence) in a buffer compatible with PTP1B activity (25 mM HEPES, pH 7.4, 125 my NaCl, 10% glycerol, 1 mM EDTA) (Doman et al., 2002). A second mixture is created identical to the above but containing 100 µM hydrocinnamic acid (Aldrich), a compound that is not a PTP1B inhibitor, in place of compound 2, and 100 µM calcein (Sigma; excitation/emmission maxima 470/509 nm; green fluorescence) in place of Texas Red.

50 µl of each of the compound mixtures is added sequentially to a solution of 1% (w/v) Span 60 and 1% (w/v) cholesterol in decane, made and held at 37° C. as example 1, whilst homogenising at 25,000 r.p.m. using an Ultra-Turrax T8 Homogenizer (IKA) with a 5 mm, dispersing tool. Homogenisation is continued for 3 minutes after the addition of the second aliquot. The coarse emulsion produced is then extruded as in example 1 to create a fine water-in-oil emulsion and incubated at 37° C. for 30 min. Inhibitors reduce the amount of non-fluorescent substrate (DiFMUP) converted to the dephosphorylated product (DiFMU; excitation/emmission maxima 358/452 nm; blue fluorescence). The water-in-oil emulsion is then converted into a water-in-oil-in water double emulsion and analysed by multi-colour flow cytometery as in example 1. Predominantly, microcapsules exhibiting green fluorescence (and containing hydrocinnamic acid) also show blue fluorescence due to dephosphorylation of DiFMUP by PTP1B. Predominantly, microcapsules exhibiting red fluorescence (and containing containing compound 2) also show little or no blue fluorescence due to inhibition of PTP1B.

Example 3

Screening of PTP1B Inhibitors from a Compound Library 100 water-in-oil emulsions are made on ice (to prevent reaction) as in example 1. The first emulsion is made by dispersing a mixture of 100 µM compound 2 (FIG. 1), which has a bis-difluoromethylene phosphonate and is a known PTP1B inhibitor (Johnson et al., 2002), the target enzyme (human recombinant PTP1B, residues 1-322; Biomol Research Laboratories, Inc.) at 5 mU/ml, the fluorogenic PTP1B substrate 6,8-difluoro-4-methylumbelliferyl phosphate (DiFMUP) (Molecular Probes), and a pre-defined ratio of Qdot™ Streptavidin Conjugates with emmission maxima at 585 nm, 655 nm and 705 nm (Quantum Dot Corporation, Hayward Calif.) in a buffer compatible with PTP1B activity (25 mM HEPES, pH 7.4, 125 mM NaCl, 10% glycerol, 1 mM EDTA) (Doman et al., 2002). The 99 other water-in-oil emulsions are identical to the above but each contain one of 99 carboxylic acids from the Carboxylic Acid Organic Building Block Library (Aldrich) in place of compound 2, and different ratios of Qdot™ Streptavidin Conjugates with emmission maxima at 585 nm, 655 nm and 705 nm. In all emulsions the concentration of the 705 nm Qdot™ Streptavidin Conjugates is 100 nM, and the concentrations of the 585 nm and 655 nm Qdot™ Streptavidin Conjugates is either 0, 11, 22, 33, 44, 55, 66, 77, 88 or 100 nM. Hence, there are 100 (10×10) permutations of Qdot™ Streptavidin Conjugate concentrations which allows the microcapsules containing each compound to have a unique fluorescence signature which is read by determining the fluorescence ratios of fluorescence at at 705 nm, 585 nm and 655 nm.

The 100 emulsions are mixed in equal ratios by vortexing and the temperature raised to 25° C. for 30 min. Inhibitors reduce the amount of non-fluorescent substrate (DiFMUP) converted to the dephosphorylated product (DiFMU; excitation/emmission maxima 358/452 nm; blue fluorescence). The water-in-oil emulsion is then converted into a water-in-oil-in water double emulsion and analysed by multi-colour flow cytometery as in example 1n. Predominantly, all microcapsules exhibited blue fluorescence due to dephosphorylation of DiFMUP by PTP1B except those with the Qdot fluorescence signature of the microcapsules containing compound 2.

Example 4

Screening of PTP1B Inhibitors from a Compound Library 100 aqueous mixtures are made on ice (to prevent reaction). The first mixture contains 100 µM compound 2 (FIG. 1), which has a bis-difluoromethylene phosphonate and is a known PTP1B inhibitor (Johnson et al., 2002), the target enzyme (human recombinant PTP1B, residues 1-322; Biomol Research Laboratories, Inc.) at 5 mU/ml, the fluorogenic PTP1B substrate 6,8-difluoro-4-methylumbelliferyl phosphate (DiFMUP) (Molecular Probes), and a pre-defined ratio of Qdot™ Streptavidin Conjugates with emmission maxima at 585 nm, 655 nm and 705 nm (Quantum Dot Corporation, Hayward Calif.) in a buffer compatible with PTP1B activity (25 mM HEPES, pH 7.4, 125 mM NaCl, 10% glycerol, 1 mM EDTA) (Doman et al., 2002). The 99 other aqueous mixtures are identical to the above but each contain one of 99 carboxylic acids from the Carboxylic Acid Organic Building Block Library (Aldrich) in place of compound 2, and different ratios of Qdot™ Streptavidin Conjugates with emission maxima at 585 nm, 655 nm and 705 nm. In all mixtures the concentration of the 705 nm Qdot™ Streptavidin Conjugates is 100 nM, and the concentrations of the 585 nm and 655 nm Qdot™ Streptavidin Conjugates is either 0, 11, 22, 33, 44, 55, 66, 77, 88 or 100 nM. Hence, there are 100 (10×10) permutations of Qdot™ Streptavidin Conjugate concentrations which allows the microcapsules containing each compound to have a unique fluorescence signature which is read by determining the fluorescence ratio of fluorescence at at 705 nm, 585 nm and 655 nm.

0.5 µl of each of the compound mixtures is added sequentially to a solution of 1% (w/v) Span 60 and 1% (w/v) cholesterol in decane, made and held at 37° C. as example 1, whilst homogenising at 25,000 r.p.m. using an Ultra-Turrax T8 Homogenizer (IKA) with a 5 mm dispersing tool. Homogenisation is continued for 3 minutes after the addition of the second aliquot. The coarse emulsion produced is then extruded as in example 1 to create a fine water-in-oil emulsion and incubated at 37° C. for 30 min. Inhibitors reduce the amount of non-fluorescent substrate (DiFMUP) converted to the dephosphorylated product (DiFMU; excitation/emmission maxima 358/452 nm; blue fluorescence). The water-in-oil emulsion is then converted into a water-in-oil-in water double emulsion and analysed by multi-colour flow cytometery as in example 1. Predominantly, all microcapsules exhibited blue fluorescence due to dephosphorylation of DiFMUP by PTP1B except those with the Qdot fluorescence signature of the microcapsules containing compound 2.

Example 5

Screening for PTP1B Inhibitors Using Microcapsules in Microfluidic Systems

Microchannels are fabricated with rectangular cross-sections using rapid prototyping in poly(dimethylsiloxane) (PDMS) (McDonald and Whitesides, 2002) and rendered hydrophobic as (Song and Ismagilov, 2003). Syringe pumps were used to drive flows (Harvard Apparatus PHD 2000 Infusion pumps). For aqueous solutions, 50 µl Hamilton Gastight syringes (1700 series, TLL) with removeable needles of 27-gaugeare used with 30-gauge Teflon tubing (Weico Wire and Cable). For the carrier fluid, 1 ml Hamilton Gastight syringes (1700 series, TLL) are used with 30-gauge Teflon needles with one hub from Hamilton (Song and Ismagilov, 2003). The carrier fluid is 9% (v/v) $C_6F_{11}C_2H_4OH$ in perfluorodecaline (PFD) (Song et al., 2003). All water-soluble reagents were dissolved in (25 mM HEPES, pH 7.4, 125 mM NaCl, 1 mM EDTA), a buffer compatible with PTP1B activity.

A solution of the target enzyme (human recombinant PTP1B, residues 1-322; Biomol Research Laboratories, Inc.) at 50 mU/ml and a solution of either a) 100 µM compound 2 (FIG. 1), which has a bis-difluoromethylene phosphonate and is a known PTP1B inhibitor (Johnson et al., 2002), or b) 100 µM hydrocinnamic acid (Aldrich), a compound that is not a PTP1B inhibitor are flowed in a microchannel as two laminar streams, with an inert centre stream (of 25 mM HEPES, pH 7.4, 125 mM NaCl, 1 mM EDTA) to separate them and prevent the enzyme and compound coming into contact prior to droplet microcapsule formation (Song et al., 2003). These three steams are continuously injected into a flow of water immiscible fluorocarbon carrier fluid (9% (v/v) $C_6F_{11}C_2H_4OH$ in PFD). Inlet channels for the aqeous solutions are 50 µm² wide and channel for PFD is 28 µm wide. A variety of PFD/water volumetric flow rates (in µl min$^{-1}$) can be used including 0.6:0.3, 1.0:0.6, 12.3:3.7, 10:6 and 20:6, resulting in flow rates of 10, 19, 190, 190 and 300 mm s$^{-1}$ respectively. Aqueous microcapsules which occupy the entire width of the channel are formed by drop-breakoff in the PFD stream (Song et al., 2003). Microcapsules containing either compound 2 or hydrocinnamic acid can be formed by switching between injection with syringes containing compound 2 and hydrocinnamic acid.

The channel immediately downstream of the point of droplet formation is winding with a peak to peak distance of 50 µm for a distance of 1 mm. This results in rapid mixing of the contents of the microcapsule by chaotic advection (Song et al., 2003). After this point the microcapsules are run for up to 1 min through a 60 cm long microchannel (to allow inhibitor binding). This microchannel is then merged with a 60×50 µm² microchannel containing aqueous microcapsules in (9% (v/v) $C_6F_{11}C_2H_4OH$ in PFD) formed as above. These larger microcapsules contain the fluorogenic PTP1B substrate 6,8-difluoro-4-methylumbelliferyl phosphate (DiFMUP) (Molecular Probes) in 25 mM HEPES, pH 7.4, 125 mM NaCl, 1 mM EDTA. After the junction between the microchannels the expanded main channel is $100 \times 50$ µm$^2$ and the microcapsules do not block the channel and can move at different speeds until a large microcapsule (containing DiFMUP) coalesces with a small microcapsule (containing PTP1B and the compound) (Song et al., 2003). The frequency of production of large and small microcapsules is equal such that each large microcapsule has a small microcapsule with which to fuse. The fused microcapsules are then run for up to 2 min through a 60 cm long microchannel. Fluorescence of the microcapsules due to production of DiFMU (excitation/emmission maxima 358/452 nm; blue fluorescence) is measured using an epifluorescence microscope. Predominantly, microcapsules exhibiting blue fluorescence are those containing hydrocinnamic acid whereas microcapsules containing compound 2 exhibit low fluorescence due to inhibition of PTP1B.

Example 6

Attachment of a Compound Library to Microbeads 5.5 µm diameter polystyrene microbeads that bear carboxylate functional groups on the surface are commercially available in an optically tagged form, as a result of incorporation of precise ratios of orange (585 nm), and red (>650 nm) fluorochromes (Fulton et al., 1997). A set of 100 such beads, each with a unique optical signature (www.luminexcorp.com) are modified with an excess of ethylenediamine and EDC (1-ethyl-3-(3-dimethylaminopropyl) carbodiimide hydrochloride (Pierce) as (Hermanson, 1996) to create primary amino groups on the surface. The photocleavable linker 4-(4-hydroxymethyl-2-methoxy-5-nitrophenoxy)butanoic acid (NovaBiochem) (Holmes and Jones, 1995) is then attached to the beads by forming an amide bond using EDC as above. 100 different carboxylic acids from the Carboxylic Acid Organic Building Block Library (Aldrich) are then coupled to the beads, by reacting with the linker alcohol to form a carboxylate ester, each of the 100 different optically tagged beads being coupled to a different carboxylic acid, and each bead being derivatised with ~10$^6$ molecules of carboxylic acid. Irradiation for 4 min on ice using a B100 AP 354 nm TV lamp (UVP) from a distance of ~5 cm results in release of the compounds from the beads as carboxylic acids.

Example 7

Screening for Inhibitors of the Enzyme Protein Tyrosine Phosphatase 1B (PTP1B) Using Compounds Attached to Microbeads PTP1B is a negative regulator of insulin and leptin signal transduction. Resistance to insulin and leptin are hallmarks of type 2 diabetes mellitus and obesity and hence PTP1B is an attractive drug target for diabetes and obesity therapy (Johnson et al., 2002). 5.5 µm diameter polystyrene microbeads that bear carboxylate functional groups on the surface are commercially available in an optically tagged form, as a result of incorporation of precise ratios of orange (585 nm), and red (>650 nm) fluorochromes (Fulton et al., 1997). (Fulton et al., 1997). First, the carboxylate functional groups on the microbeads are converted to primary amines using ethylenediamine and EDC as in example 6. A phosphopeptide substrate for PTP1B, the undecapaptide EGFR$_{988-998}$ (DADEpYLIPQQG) (Zhang et al., 1993), is then coupled to both sets of microbeads via the surface amino groups using EDC. This peptide is made by solid phase synthesis on Sieber Amide resin (9-Fmoc-amino-xanthen-3-yloxy-Merrifield resin) (Novabiochem) with orthogonal protection on the side chain carboxylate groups using carboxylate-O-allyl esters. A linker comprised of tetradecanedioic acid is coupled to the N-terminus and the peptide cleaved from the beads using 1% TFA to yield a peptide with a C-terminal amide The peptide is coupled to the beads (using EDC) via the linker to give ~10$^5$ peptides per bead. The remaining surface amino groups are then modified by attaching the photochemically cleavable linker 4-(4-hydroxymethyl-2-methoxy-5-nitrophenoxy)butanoic acid as in example 6. The protecting groups on the side chain carboxylates of the peptide are then removed using $Pd(Ph_3)_4/CHCl_3/HOAc/N$-methyl morpholine. A first set of microbeads is derivatised with 3-(4-difluorophosphonomethylphenyl)propanoic acid (compound 1, FIG. 1), a compound that is a known PTP1B inhibitor (Johnson et al., 2002). A second set of beads, with a distinct optical tag from the first set of beads, is derivatised with hydrocinnamic acid (Aldrich), a compound that is not a PTP1B inhibitor. In each case the compound is coupled by reacting with the linker alcohol to form a carboxylate ester as in example 6. Each microbead is derivatised with ~10$^6$ molecules (Fulton et al., 1997).

Figure 2:
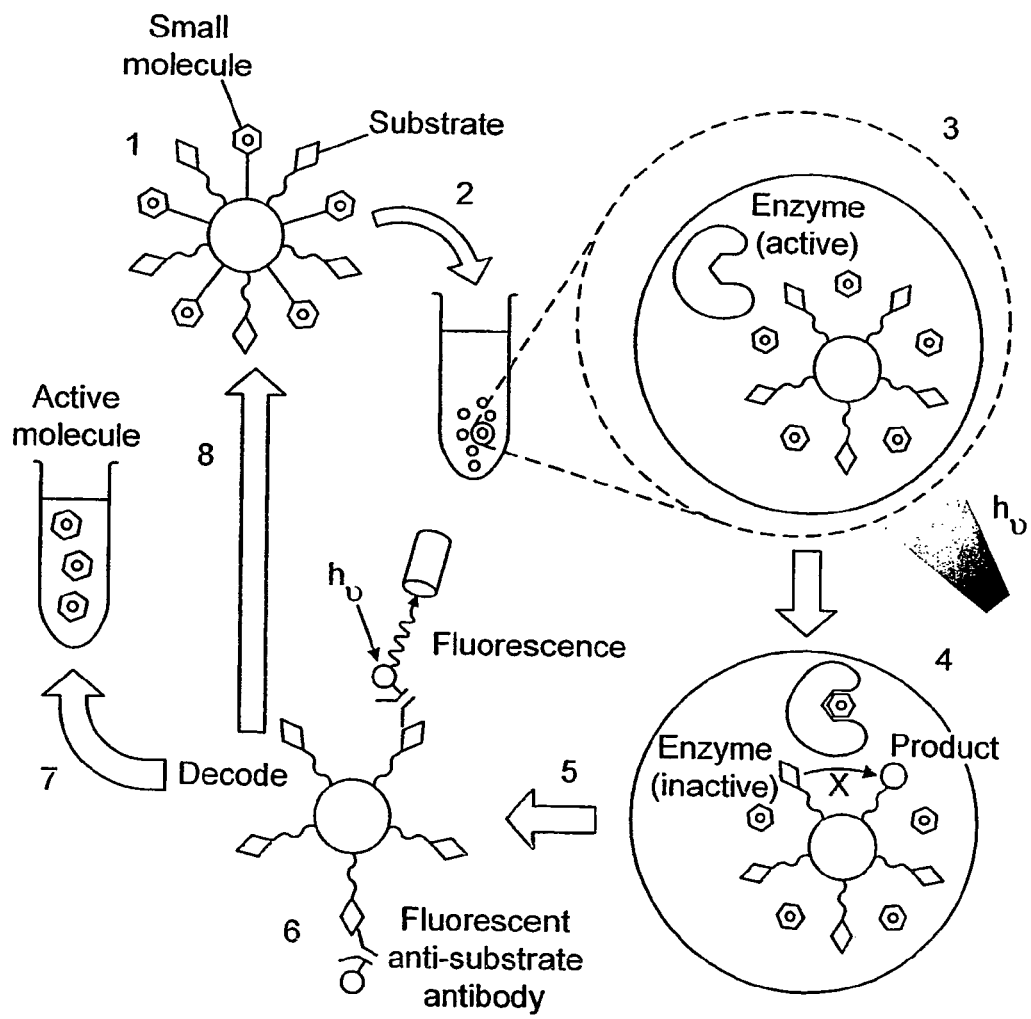
FIG. 2. Screening PTP1B inhibitors using IVC. Polystyrene beads with surface carboxylate groups, died with orange or red fluorochromes (Fulton et al., 1997), are derivatised with a phosphopeptide PTP1B substrate, and either PTP1B inhibitors or non-inhibitory compounds, attached via a cleavable linker (1). After mixing the beads, single beads and target enzyme (PTP1B) are colocalised in a microcompartment by forming a water-in-oil emulsion (2). The compound is released (photochemically) (3). Inhibitors reduce the amount of substrate converted to product (dephosphorylated peptide) (4). The enzyme reaction is stopped and the emulsion is broken (5). After labelling with green fluorescent anti-substrate antibodies, beads are analysed by 3-colour flow cytometry to simultaneously determine extent of inhibition and the compound on the beads (6). Compound libraries can be coupled to optically tagged beads (see below) and rapidly decoded by flow cytometry (at up to 100,000 beads $s^{-1}$). Hit compounds are re-synthesised for further characterisation (7) or elaborated and rescreened in a process of synthetic evolution (8).
Figure 3:
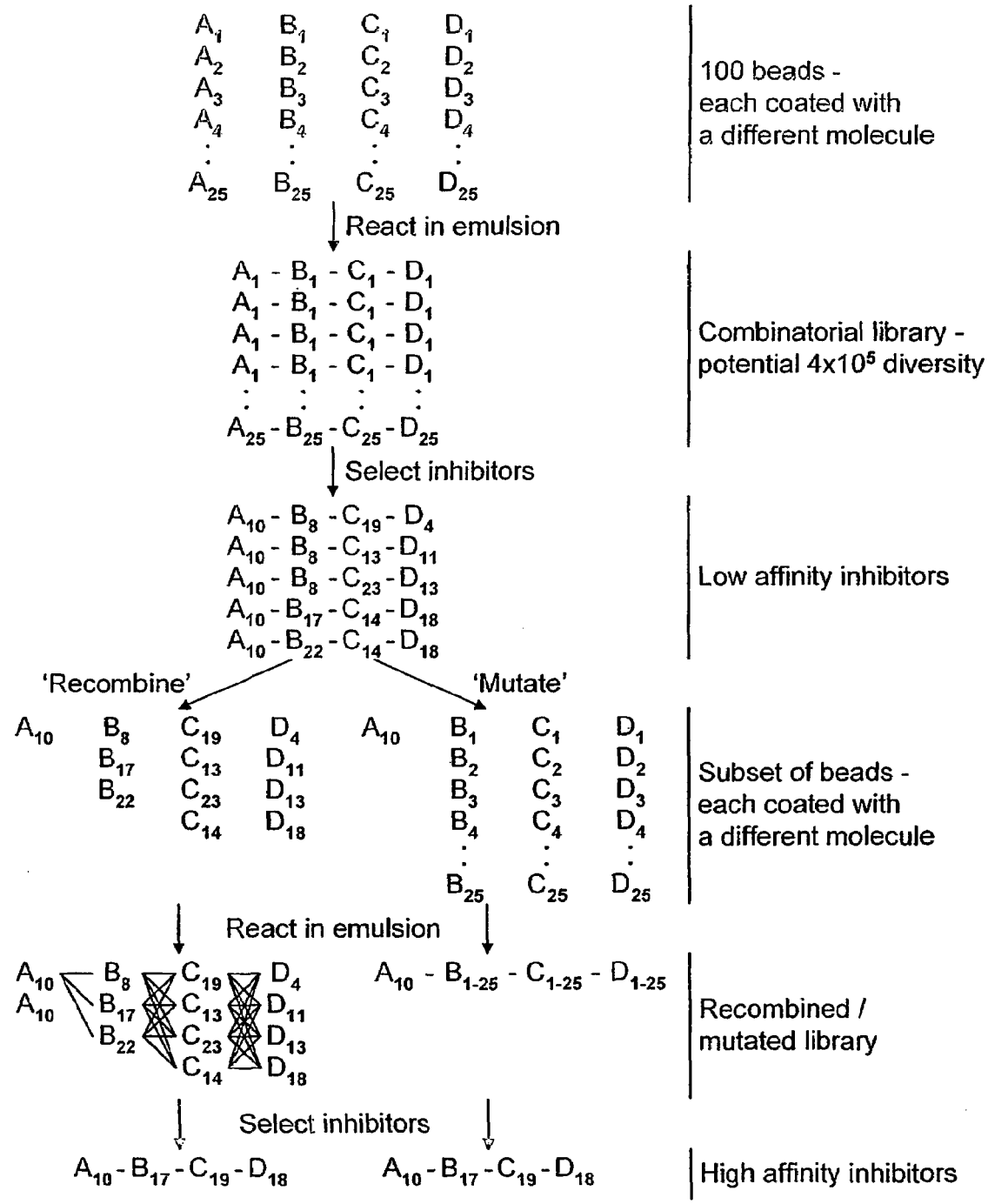
FIG. 3. Synthesising PTP1B Inhibitors in an emulsion. Two types of beads are created, differentially labelled with orange and red fluorochromes, and derivatised with two types of molecule, A or B (neither, one, or both of which contain a difluoromethylene phosphonate moiety), attached via a reversible connection (a Schiff base). Beads are emulsified to give, on average, two beads per compartment. The molecules, A & B, are released from the beads in the compartment and react to form a new molecule, A-B, (in solution). If A-B is a PTP1B inhibitor the PTP1B substrate also on the beads is not dephosphorylated and these beads identified by flow cytometry as FIG. 2.
Figure 4:
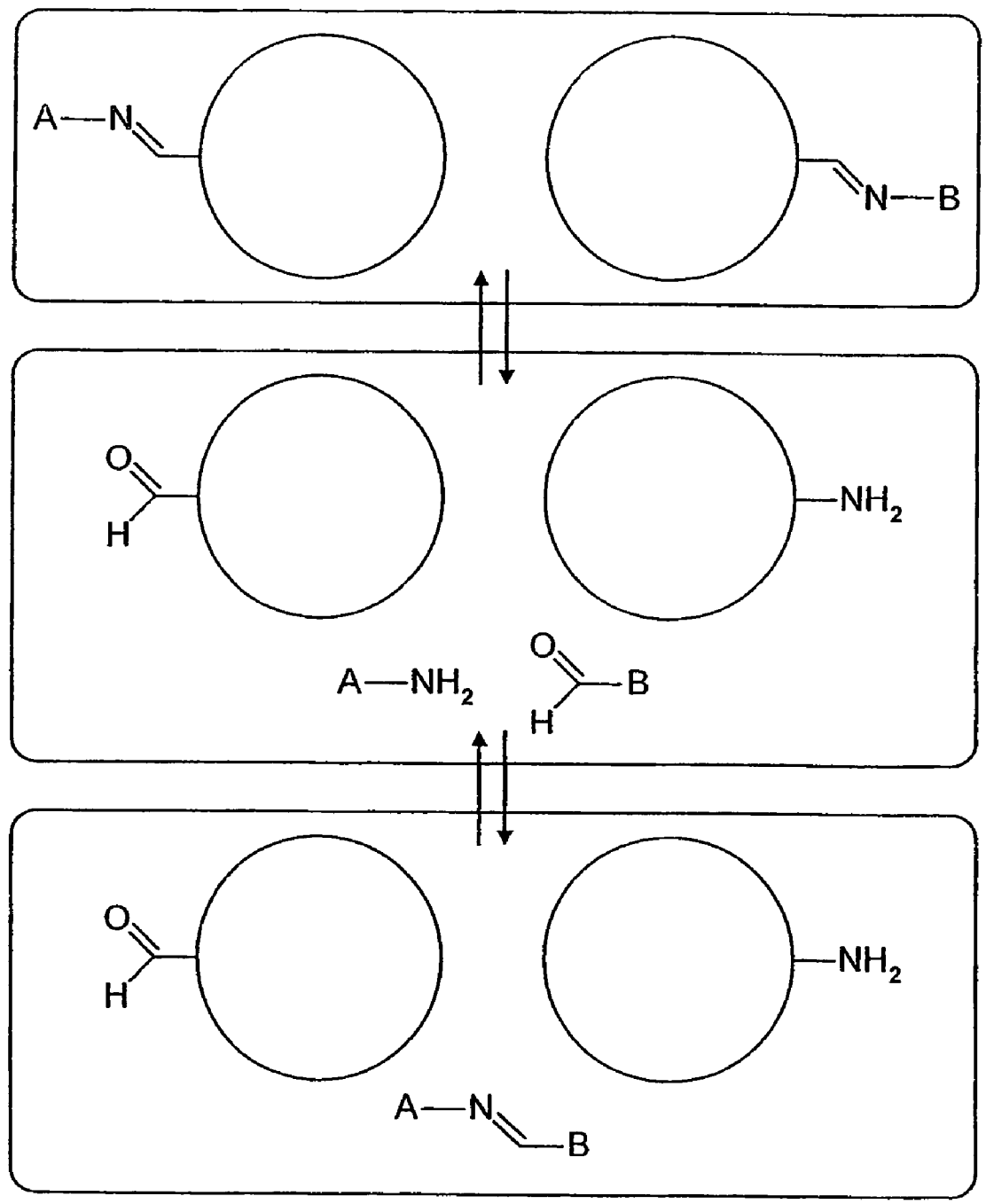
FIG. 4. Small molecule evolution using four-component reactions. Four sets of 25 beads are created, each derivatised with one of 25 variants of molecules A, B, C or D, emulsified to give, on average, 4 beads per compartment, the compounds released to synthesise a large combinatorial repertoire ($4 \times 10^5$) in situ and screened as FIG. 2. Low affinity inhibitors will be 'recombined' by re-screening mixtures of beads carrying moieties identified in inhibitors. Beads carrying a moiety found in inhibitors (e.g. $A_{10}$) can also be mixed with complete sets of beads coated with B, C and D and screened. If a moiety (say $B_8$) is then identified as a component of an inhibitor, beads coated with $A_{10}$ and $B_8$ can be mixed with complete sets of beads C and D and the process repeated. This process of 'mutation' also results in deconvolution. After fixing three of the four moieties in active compounds, deconvolution can be completed using multiplex bead analysis as above. Compounds can be re-diversified or 'mutated' using bead sets carrying variant, exploded sets of the molecules used in the original libraries.

The microbeads are then screened using the method outlined in FIG. 2. The two sets of microbeads are mixed in ratios varying from 1:1000 to 1:1 (compound 1 beads: hydrocinnamic acid beads) and 10$^8$ total microbeads are mixed with the target enzyme (human recombinant PTP1B, residues 1-322; Biomol Research Laboratories, Inc.) at a concentration of 10 nM, on ice (to prevent reaction) in a buffer compatible with PTP1B activity (25 mM HEPES, pH 7.4, 125 mM NaCl, 10% glycerol, 1 mM EDTA) (Doman et al., 2002). Single beads and target enzyme (PTP1B) are then colocalised in microcapsules by forming a water-in-oil emulsion (also on ice). The concentration of beads is such that most microcapsules contain one or no beads. The compound is released photochemically (as in example 6) and the temperature raised to 25° C. Inhibitors reduce the amount of substrate converted to product (dephosphorylated peptide). The emulsion is cooled to 4° C. and broken as (Griffiths and Tawfik, 2003) into 100 µM vanadate to stop the reaction (Harder et al., 1994). After labelling with an anti-substrate (anti-phosphotyrosine) antibody labelled with the green (530 nm) fluorochrome fluorescein isothiocyanate (mouse monoclonal IgG$_{2b}$ PY20 (Santa Cruz) according to the manufacturer's instructions, beads are analysed by 3-colour flow cytometry using a FACScan (Becton-Dickinson), FACScalibur (Becton-Dickinson) or MoFlo (Cytomation) flow cytometers to simultaneously determine the extent of inhibition and the compound on the beads. Predominantly, dephosphorylation of the peptide is only observed on those microbeads which were coated with PTP1B inhibitors, and not on other microbeads.

Example 8

Screening of PTP1B Inhibitors from a Compound Library Attached to Microbeads

A set of 100 5.5 µm diameter polystyrene microbeads, bearing carboxylate functional groups on the surface and each with a unique optical signature as a result of incorporation of precise ratios of orange (585 nm), and red (>650 nm) fluorochromes (Fulton et al., 1997) are derivatised with a phosphopeptide substrate for PTP1B, the undecapaptide EGFR$_{988-998}$ (DADEpYLIPQQG) (Zhang et al., 1993), and 100 different carboxylic acids, each attached via a photochemically cleavable linker, as in example 7. One of these carboxylic acids is 3-(4-difluorophosphonomethylphenyl) propanoic acid (compound 1, FIG. 1), a compound that is a known PTP1B inhibitor (Johnson et al., 2002). The other 99 carboxylic acids are from the Carboxylic Acid Organic Building Block Library (Aldrich) as example 6. Equal numbers of each of the 100 bead sets are then mixed and screened as for example 7. Predominantly, dephosphorylation of the peptide is only observed on those microbeads which were coated with the PTP1B inhibitor 3-(4-difluorophosphonomethylphenyl) propanoic acid (compound 1, FIG. 1), and not on microbeads coated with other compounds.

Example 9

Synthesis of secondary Compounds in Emulsion Microcapsules and Screening for PTP1B Inhibition in Microfluidic Systems Microchannels are fabricated with rectangular cross-sections using rapid prototyping in poly(dimethylsiloxane) (PDMS) (McDonald and Whitesides, 2002) and rendered hydrophobic as (Song and Ismagilov, 2003). Syringe pumps were used to drive flows (Harvard Apparatus PHD 2000 Infusion pumps). For aqueous solutions, 50 μl Hamilton Gastight syringes (1700 series, TLL) with removeable needles of 27-gaugeare used with 30-gauge Teflon tubing (Weico Wire and Cable). For the carrier fluid, 1 ml Hamilton Gastight syringes (1700 series, TLL) are used with 30-gauge Teflon needles with one hub from Hamilton (Song and Ismagilov, 2003). The carrier fluid is 9% (v/v) $C_6F_{11}C_2H_4OH$ in perfluorodecaline (PFD) (Song et al., 2003). All water-soluble reagents were dissolved in (25 mM HEPES, pH 7.4, 125 mM NaCl, 1 mM EDTA), a buffer compatible with PTP1B activity.

A solution of the target enzyme (human recombinant PTP1B, residues 1-322; Biomol Research Laboratories, Inc.) at 50 mU/ml, a solution of a compound which is a primary amine, and a solution of a compound which is an aldehyde are flowed in a microchannel as three laminar streams, with two inert separating streams (of 25 mM HEPES, pH 7.4, 125 mM NaCl, 1 mM EDTA) to prevent the enzyme and the compounds coming into contact prior to droplet microcapsule formation (Song et al., 2003). These five streams are continuously injected into a flow of water immiscible fluorocarbon carrier fluid (9% (v/v) $C_6F_{11}C_2H_4OH$ in PFD). The amines and aldehydes can either a) contain a difluoromethylene phosphonate moiety (FIG. 6, compounds A and B), or b) contain no difluoromethylene phosphonate moiety.

Inlet channels for the aqeous solutions are 50 μm$^2$ wide and the channel for PFD is 28 μm wide. A variety of PFD/water volumetric flow rates (in μl min$^{-1}$) can be used including 0.6:0.3, 1.0:0.6, 12.3:3.7, 10:6 and 20:6, resulting in flow rates of 10, 19, 190, 190 and 300 mm s$^{-1}$ respectively. Aqueous microcapsules which occupy the entire width of the channel are formed by drop-breakoff in the PFD stream (Song et al., 2003). Microcapsules containing compounds with and without difluoromethylene phosphonate moieties can be formed by switching between injection with syringes containing amines or aldehydes with or without a difluoromethylene phosphonate moiety.

The channel immediately downstream of the point of droplet formation is winding with a peak to peak distance of 50 μm for a distance of 1 mm. This results in rapid mixing of the contents of the microcapsule by chaotic advection (Song et al., 2003). After this point the microcapsules are run for up to 1 min through a 60 cm long microchannel. This allows the amine and the aldehyde to react together by formation of a Schiff base to create a secondary compound and allows inhibitors to bind to PTP1B. This microchannel is then merged with a 60×50 μm$^2$ microchannel containing aqueous microcapsules in (9% (v/v) $C_6F_{11}C_2H_4OH$ in PFD) formed as above. These larger microcapsules contain the fluorogenic PTP1B substrate 6,8-difluoro-4-methylumbelliferyl phosphate (DiFMUP) (Molecular Probes) in 25 mM HEPES, pH 7.4, 125 mM NaCl, 1 mM EDTA. After the junction between the microchannels the expanded main channel is 100×50 μm$^2$ and the microcapsules do not block the channel and can move at different speeds until a large microcapsule (containing DiFMUP) coalesces with a small microcapsule (containing PTP1B and the compound) (Song et al., 2003). The frequency of production of large and small microcapsules is equal such that each large microcapsule has a small microcapsule with which to fuse. The fused microcapsules are then run for up to 2 min through a 60 cm long microchannel. Fluorescence of the microcapsules due to production of DiFMU (excitation/emmission maxima 358/452 nm; blue fluorescence) is measured using an epifluorescence microscope.

Figure 6:
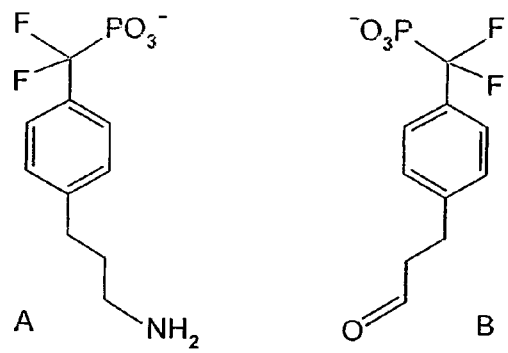
FIG. 6. Primary compounds for the synthesis of PTP1B inhibitors. An amine (A) and an aldehyde (B) with difluoromethylene phosphonate moieties. Amine A reacts with aldehyde B in the aqueous microcapsules of a water-in-oil emulsion to generate the imine (C which is a potent PTP1B inhibitor. C can be reduced in situ using cyanoborohydride to generate the stable amine D.
Figure 6:
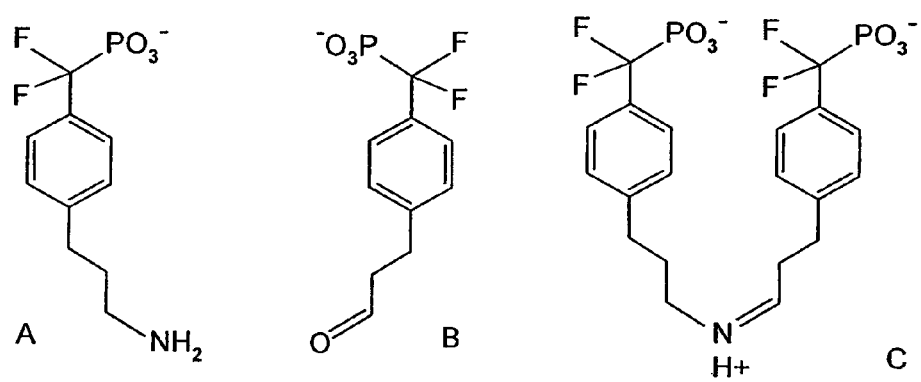
Figure 6:
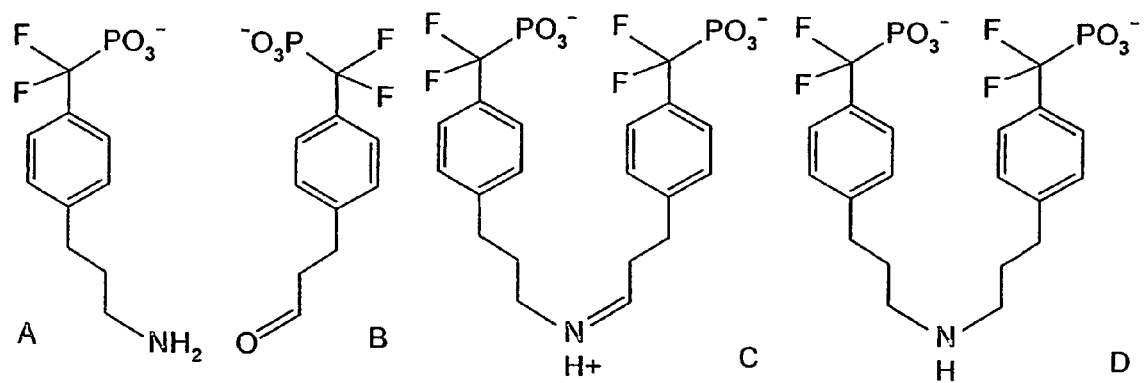

Predominantly, when the amine and aldehyde concentrations are low (<100 μM) inhibition of PTP1B activity is only observed in microcapsules containing both an amine with a difluoromethylene phosphonate moiety (compound A, FIG. 6) and an aldehyde with a difluoromethylene phosphonate moiety (compound B, FIG. 6). This is because the Schiff base formed in these microcapsules (compound C, FIG. 6) contains bis-difluoromethylene phosphonate and is a much more potent PTP1B inhibitor than a molecule with a single difluoromethylene phosphonate moiety (see FIG. 1).

Predominantly, when the amine and aldehyde concentrations are high (>100 μM) inhibition of PTP1B activity is observed in microcapsules containing either an amine with a difluoromethylene phosphonate moiety (compound A, FIG. 6) or an aldehyde with a difluoromethylene phosphonate moiety (compound B, FIG. 6), or both, but not in other microcapsules. This is because at higher concentrations molecules with either a single difluoromethylene phosphonate moiety or a bis-difluoromethylene phosphonate (compound C, FIG. 6) can inhibit PTP1B (see FIG. 1).

Example 10

Synthesis of Secondary Compounds in Emulsion Microcapsules and Screening for PTP1B Inhibition Using Compounds Attached to Microbeads 5.5 μm diameter polystyrene microbeads that bear carboxylate functional groups on the surface are commercially available in an optically tagged form, as a result of incorporation of precise ratios of orange (585 nm), and red (>650 nm) fluorochromes (Fulton et al., 1997). First, the carboxylate functional groups on the microbeads are converted to primary amines using ethylenediamine and EDC as in example 6. A phosphopeptide substrate for PTP1B, the undecapaptide EGFR$_{988-998}$ (DADEpYLIPQQG) (Zhang et al., 1993), is then coupled to both sets of microbeads via the surface amino groups using EDC and the protecting groups on the side chain carboxylates of the peptide removed as in example 7. A first set of microbeads (set 1) is reacted with succinimidyl p-formylbenzoate to convert the surface amino groups to aldehydes. A second set of microbeads (set 2), with a distinct optical tag from the first set of microbeads, is left unreacted (i.e. with primary amines on the surface).

The first set of microbeads (set 1), are then reacted with a compound containing a difluoromethylene phosphonate moiety and a primary amine (compound A, FIG. 6) via reaction with the surface aldehyde groups to form a Schiff base. The second set of microbeads (set 2), with a distinct optical tag from the first set of beads, are reacted with a compound containing a difluoromethylene phosphonate moiety and an aldehyde (compound B, FIG. 6) via reaction of the aldehyde with the surface amine groups to form a Schiff base. The formation of Schiff bases is enhanced by reaction at alkaline pH (i.e. pH9-10). Microbeads coated with compounds at various densities are created.

The two sets of microbeads are mixed with the target enzyme (human recombinant PTP1B, residues 1-322; Biomol Research Laboratories, Inc.) at a concentration of 10 nM, on ice (to prevent reaction) in a buffer compatible with PTP1B activity (25 mM HEPES, pH 7.4, 125 mM NaCl, 10% glycerol, 1 mM EDTA) (Doman et ad., 2002). The beads and target enzyme (PTP1B) are immediately compartmentalised in microcapsules by forming a water-in-oil emulsion (also on ice).

The number of microbeads is varied such that, at one extreme, most microcapsules contain one or no beads, and at the other, the majority of microcapsules contain two or more microbeads. The temperature raised to 25° C. The Schiff base is a relatively labile, reversible interaction, readily hydrolysed at neutral pH, resulting in release of compounds from the beads. In microcapsules containing a microbead from both set 1 and set 2, the compounds released from the microbeads can react with each other, forming a Schiff base and creating a new molecule in solution. This new molecule (FIG. 6, compound C) contains a bis-difluoromethylene phosphonate moiety and has significantly more potency as a PTP1B inhibitor than compounds with a single difluoromethylene phosphonate moiety (see FIG. 1). Inhibitors reduce the amount of substrate converted to product (dephosphorylated peptide). The emulsion is cooled to 4° C. and broken as (Griffiths and Tawfik, 2003) into 100 μM vanadate to stop the reaction (Harder et al., 1994). After labelling with an anti-substrate (anti-phosphotyrosine) antibody labelled with the green (530 nm) fluorochrome fluorescein isothiocyanate (mouse monoclonal IgG$_{2b}$ PY20 (Santa Cruz) according to the manufacturer's instructions, beads are analysed by 3-colour flow cytometry using a FACScan (Becton-Dickinson), FACScalibur (Becton-Dickinson) or MoFlo (Cytomation) flow cytometers to simultaneously determine the extent of inhibition and the compound on the beads. With low microbead numbers, most microcapsules contain only a single or no microbeads and PTP1B inhibition is only detected on beads coated with a high density of inhibitor, when the concentration of inhibitor released into solution in each microcapsule is sufficiently high for effective inhibition. In contrast, when the bead numbers are higher, many microbeads are detected where little substrate has been converted to product, even when the microbeads are coated with inhibitor at low density. This is due to the formation of a highly potent PTP1B inhibitor (FIG. 6, compound C) containing a bis-difluoromethylene phosphonate moiety in microcapsules containing a microbead each from set 1 and set 2.

Example 11

Synthesis of a Library 2500 Secondary Compounds in Emulsion Microcapsules and Screening for PTP1B Inhibition Using Compounds Attached to Microbeads A set of 100 5.5 μm diameter polystyrene microbeads, bearing carboxylate functional groups on the surface and each with a unique optical signature as a result of incorporation of precise ratios of orange (585 nm), and red (>650 nm) fluorochromes (Fulton et al., 1997) are modified to convert the carboxylate functional groups to primary amines as in example 6, then derivatised with a phosphopeptide substrate for PTP1B, the undecapeptide EGFR$_{988-998}$ (DADEpYLIPQQG) (Zhang et al., 1993), as in example 10. The first 50 sets of microbeads are reacted to convert a proportion of the surface carboxyl groups to aldehydes as in example 10. The second 50 sets of microbeads are left unreacted (i.e. with primary amines on the surface).

The first 50 sets of microbeads are each reacted with a unique compound containing a primary amine via reaction with the surface aldehyde groups to form a Schiff base which links the compounds to the beads. One of these compounds (compound A, FIG. 6) contains a difluoromethylene phosphonate moiety. The second 50 sets of microbeads are each reacted with a unique compound containing an aldehyde via reaction with the surface amine groups to form a Schiff base which links the compounds to the beads. One of these compounds (compound B, FIG. 6) contains a difluoromethylene phosphonate moiety. The formation of Schiff bases is enhanced by reaction at alkaline pH (i.e. pH9-10).

The two sets of microbeads are mixed with the target enzyme (human recombinant PTP1B, residues 1-322; Biomol Research Laboratories, Inc.) at a concentration of 10 nM, on ice (to prevent reaction) in a buffer compatible with PTP1B activity (25 mM HEPES, pH 7.4, 125 mM NaCl, 10% glycerol, 1 mM EDTA) (Doman et al., 2002). The beads and target enzyme (PTP1B) are immediately compartmentalised in microcapsules by forming a water-in-oil emulsion (also on ice).

The number of microbeads is such that the modal number of microcapsules per microcapsule is two. The temperature raised to 25° C. The Schiff base is a relatively labile, reversible interaction, readily hydrolysed at neutral pH, resulting in release of compounds from the beads. In microcapsules containing a microbead from one of the first 50 sets and a microbead from one of the second 50 sets, the compounds released from the microbeads can react with each other, forming a Schiff base and creating a new molecule in solution. Inhibitors reduce the amount of substrate converted to product (dephosphorylated peptide). The emulsion is cooled to 4° C. and broken as (Griffiths and Tawfik, 2003) into 100 μM vanadate to stop the reaction (Harder et al., 1994). After labelling with an anti-substrate (anti-phosphotyrosine) antibody labelled with the green (530 nm) fluorochrome fluorescein isothiocyanate (mouse monoclonal IgG$_{2b}$ PY20 (Santa Cruz) according to the manufacturer's instructions, beads are analysed by 3-colour flow cytometry using a FACScan (Becton-Dickinson), FACScalibur (Becton-Dickinson) or MoFlo (Cytomation) flow cytometers to simultaneously determine the extent of inhibition and the compound on the beads. Beads which were coated with a primary compound which is itself a PTP1B inhibitor, or which reacts with another primary compound released from another co-compartmentalised bead to form a second inhibitor are identified as little substrate has been converted to product. The identified beads where as little substrate has been converted to product include those carrying compounds containing a difluoromethylene phosphonate moiety. When the microbeads are coated with compounds at low density the concentration of the released compounds containing a difluoromethylene phosphonate moieties in the microcapsules is insufficient to efficiently inhibit PTP1B (see example 7). However in microcapsules containing two microbeads, one from the first set of 50 beads and one from the second set of 50 beads, and where each microbead carries a molecule with a difluoromethylene phosphonate moiety, the released molecules can form a highly potent PTP1B inhibitor (compound C, FIG. 6) containing a bis-difluoromethylene phosphonate moiety in the microcapsules which inhibits conversion of the PTP1B substrate to product.

Example 12

Compartmentalisation of Small Molecules in a Water-in-Fluorocarbon Emulsions

Figure 5:
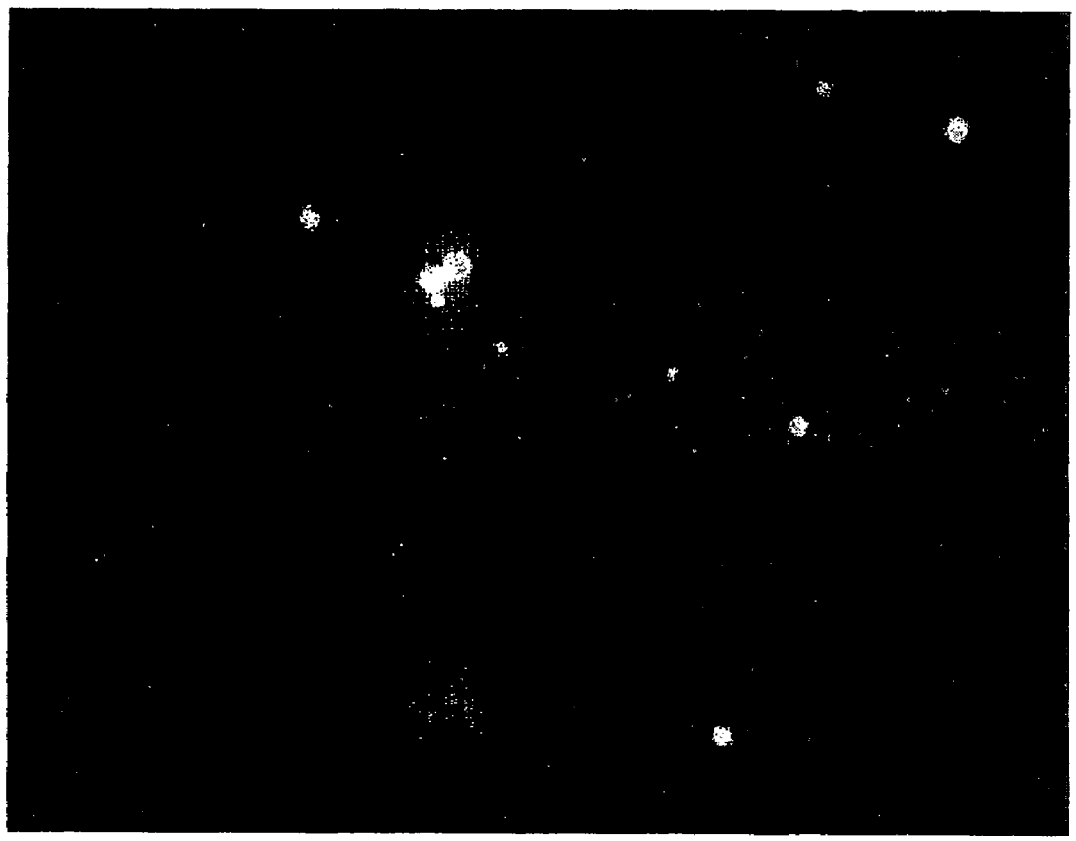
FIG. 5. Compartmentalisation of small molecules in water-in-fluorocarbon emulsions. Water-in-perfluorooctyl bromide emulsions were made containing texas red (1 mM) and calcein (1 mM) in the aqueous phase by homogenisation as described in example 6 The two emulsions were mixed by vortexing and imaged by epifluorescence microscopy after 24 hours. No exchange of texas-red (red fluorescence) and calcein (green fluorescence) between microdroplets could be observed.

Water-in-fluorocarbon emulsions containing 95% (v/v) perfluorooctyl bromide, 5% (v/v) phosphate buffered saline containing the molecule of interest in solution, and 2% (w/v) $C_8F_{17}C_{11}H_{22}OP(O)[N(CH_2CH_2)_2O]_2$ (F8H11DMP) as surfactant were formed essentially as (Sadtler et al., 1996) by extrusion (15 times) through 14 μm filters (Osmonics) or by homogenising for 5 min at 25,000 r.p.m. using an Ultra-Turrax T8 Homogenizer (IKA) with a 5 mm dispersing tool. Emulsions were made containing a series of small fluorescent molecules dissolved in the aqueous phase at concentrations from 100 μm to 2 mM. These molecules, including calcein, texas red, fluorescein, coumarin 102, 7-hydroxycoumarin-3-carboxylic acid and 7-diethylamino-4-methyl coumarin (coumarin 1), had molecular weights from 203 to 625 Da and Log P values—calculated using SRC's LogKow/KowWin Program (Meylan and Howard, 1995)—ranging from –0.49 to 4.09. Emulsions containing different coloured fluorochromes were mixed by vortexing. Compartmentalisation was observed by epifluorescence microscopy of the mixed emulsions. No exchange between compartments was observed 24 hours after mixing (see FIG. 5).

REFERENCES

Adang, A. E., and Hermkens, P. H. (2001). The contribution of combinatorial chemistry to lead generation: an interim analysis. Curr Med Chem 8, 985-998.
Anderson, J. E. (1993). Restriction endonucleases and modification methylases. Curr Op Struct Biol 3, 24-30.
Becher, P. (1957) *Emulsions: theory and practice*. Reinhold, N.Y.
Benita, S. (ed.). (1996) *Microencapsulation: methods and industrial applications*. Marcel Dekker, New York.
Bernath, K., Hai, M., Mastrobattista, E., Griffiths, A. D., Magdassi, S. and Tawfik, D. S. (2004) In vitro compartmentalization by double emulsions: sorting and gene enrichment by fluorescence activated cell sorting. Anal Biochem, 325, 151-157.
Bru, R. and Walde, P. (1991) Product inhibition of alpha-chymotrypsin in reverse micelles. Eur J Biochem, 199, 95-103.
Bru, R. and Walde, P. (1993) Catalytic activity of elastase in reverse micelles. Biochem Mol Biol Int, 31, 685-692.
Burbaum, J. (1998). Miniaturization technologies in HTS: how fast, how small, how soon? Drug Discov Today 3, 313-322.
Calvert, P. (2001) Inkjet printing for materials and devices. Chem. Mater., 13, 3299-3305.
Chakrabarti, A. C., Breaker, R. R., Joyce, G. F. and Deamer, D. W. (1994) Production of RNA by a polymerase protein encapsulated within phospholipid vesicles. J Mol Evol, 39, 555-559.
Chang, T. M. (1987) Recycling of NAD(P) by multienzyme systems immobilized by microencapsulation in artificial cells. Methods Enzymol, 136, 67-82.
Chang, T. M. S. (1992) Recent advances in artificial cells based on microencapsulation. In Donbrow, M. (ed.), *Microcapsules and nanoparticles in medicine and pharmacy*. CRC Press, Boca Raton, Fla., pp. 323-339.
Creagh, A. L., Prausnitz, J. M. and Blanch, H. W. (1993) Structural and catalytic properties of enzymes in reverse micelles. Enzyme Microb Technol, 15, 383-392.
Curran, D. P. (1998) Strategy-level separations in organic synthesis: from planning to practice. Angew Chem Int Ed, 37, 1174-1196.
Czarnik, A. W. (1997). Encoding methods for combinatorial chemistry. Curr Opin Chem Biol 1, 60-66.
Davis, S. S., and Walker, I. M. (1987). Multiple emulsions as targetable delivery systems. Methods in Enzymology 149, 51-64.
de Gans, B.-J., Duineveld, P. C. and Schubert, U. S. (2004) Inkjet printing of polymers: state of the art and future developments. Advanced materials, 16, 203-213.
Dickinson, E. (1994) Emulsions and droplet size control. In Wedlock, D. J. (ed.), *Controlled particle, droplet and bubble formation*. Butterworth-Heinemann, Oxford, pp. 191-257.
Doi, N., and Yanagawa, H. (1999). STABLE: protein-DNA fusion system for screening of combinatorial protein libraries in vitro. FEBS Lett 457, 227-230.
Doman, T. N., McGovern, S. L., Witherbee, B. J., Kasten, T. P., Kurumbail, R., Stallings, W. C., Connolly, D. T. and Shoichet, B. K. (2002) Molecular docking and high-throughput screening for novel inhibitors of protein tyrosine phosphatase-1B. J Med Chem, 45, 2213-2221.
Finch, C. A. (1993) Encapsulation and controlled release. Spec. Publ.—R. Soc. Chem., 138, 35.
Fornusek & Vetvicka, Crit Rev Ther Drug Carrier Syst. 1986; 2(2):137-74
Fu, A. Y., Chou, H. P., Spence, C., Arnold, F. H. and Quake. S. R. (2002) An integrated microfabricated cell sorter. Anal Chem, 74, 2451-2457.
Fulton, R. J., McDade, R. L., Smith, P. L., Kienker, L. J. and Kettman, J. R., Jr. (1997) Advanced multiplexed analysis with the FlowMetrix system. Clin Chem, 43, 1749-1756.
Ghadessy, F. J., Ong, J. L. and Holliger, P. (2001) Directed evolution of polymerase function by compartmentalized self-replication. Proc Natl Acad Sci USA, 98, 4552-4557.
Gordon, K., and Balasubramanian, S. (1999). Solid phase chemistry-designer linkers for combinatorial chemistry. J Chem Technol Biotechnol 74, 835-851.
Griffiths, A. D., Williams, S. C., Hartley, O., Tomlinson, I. M., Waterhouse, P., Crosby, W. L., Kontermann, R. E., Jones, P. T., Low, N. M., Allison, T. J., and et al. (1994). Isolation of high affinity human antibodies directly from large synthetic repertoires. Embo J 13, 3245-3260.
Griffiths, A. D. and Tawfik, D. S. (2003) Directed evolution of an extremely fast phosphotriesterase by in vitro compartmentalization. Embo J, 22, 24-35.

Guixe et al., Ligand-induced conformational transitions in *Escherichia coli* phosphofructokinase 2: evidence for an allosteric site for MgATP2-. Biochemistry. Sep. 22, 1998; 37(38):13269-75.

Haber, J., Maslakiewicz, P., Rodakiewicz, N. J. and Walde, P. (1993) Activity and spectroscopic properties of bovine liver catalase in sodium bis(2-ethylhexyl)sulfosuccinate/isooctane reverse micelles. *Eur J Biochem,* 217, 567-573.

Han, M., Gao, X., Su, J. Z., and Nie, S. (2001). Quantum-dot-tagged microbeads for multiplexed optical coding of biomolecules. Nat Biotechnol 19, 631-635.

Han, M., Gao, X., Su, J. Z. and Nie, S. (2001) Quantum-dot-tagged microbeads for multiplexed optical coding of biomolecules. *Nat Biotechnol,* 19, 631-635.

Handen, J. S. (Summer 2002). High-throughput screening-challenges for the future. Drug Discov World, 47-50.

Harder, K. W., Owen, P., Wong, L. K., Aebersold, R., Clark-Lewis, I., and Jirik, F. R. (1994). Characterization and kinetic analysis of the intracellular domain of human protein tyrosine phosphatase beta (HPTP beta) using synthetic phosphopeptides. Biochem J 298 (Pt 2), 395-401.

Heim R, Tsien R Y. Engineering green fluorescent protein for improved brightness, longer wavelengths and fluorescence resonance energy transfer. Curr Biol. Feb. 1, 1996; 6(2): 178-82.

Hergenrother. P. J., Depew, K. P. and Schreiber, S. L. (2000). Small-molecule microarrays: covalent attachment and screening of alcohol-containing small molecules on glass slides. J Am Chem Soc 122, 7849-7850.

Hermanson, G. T. (1996) *Bioconjugate techniques.* Academic Press, San Diego.

Hildebrand, J. H. and Cochran, D. F. R. (1949) *J. Am. Chem. Soc.,* 71, 22.

Hochuli, E., Dobeli, H., and Schacher, A. (1987). New metal chelate adsorbent selective for proteins and peptides containing neighbouring histidine residues. J Chromatogr 411, 177-184.

Holmes, C. P., and Jones, D. G. (1995). Reagents for combinatorial organic synthesis: development of a new o-nitrobenzyl photolabile linker for solid phase synthesis. J Org Chem 60, 2318-2319.

Hudlicky, M. (1992) *Chemistry of Organic Fluorine Compounds.* Ellis Horwood, New York.

Johannsson, A. (1991). Heterogeneous enzyme immunoassays. In Principles and practice of immunoassays, C. P. Price, and D. J. Newman, eds. (New York, Stockton Press), pp. 295-325.

Johannsson, A., and Bates, D. L. (1988). Amplification by second enzymes. In ELISA and other solid phase immunoassays, D. M. Kemeny, and S. J. Challacombe, eds. (Chichester, John Wiley), pp. 85-106.

Johnson, T. O., Ermolieff, J., and Jirousek, M. R. (2002). Protein tyrosine phosphatase 1B inhibitors for diabetes. Nature Reviews Drug Discovery 1, 696-709.

Keij et al., Cytometry. Mar. 1, 1995; 19(3):209-16

Kerker, Cytometry. July 1983; 4(1):1-10

Klug, A. (1995). Gene regulatory proteins and their interaction with DNA. Ann N Y Acad Sci 758, 143-160.

Klug, A., and Schwabe, J. W. (1995). Protein motifs 5. Zinc fingers. Faseb J 9, 597-604.

Krafft, M. P., Chittofrati, A. and Riess, J. G. (2003) Emulsions and microemulsions with a fluorocarbon phase. *Curr. Op. Colloid Interface Sci.,* 8, 251-258.

Kumar, A., Kumar, A. and Katiyar, S. S. (1989) Activity and kinetic characteristics of glutathione reductase in vitro in reverse micellar waterpool. *Biochim Biophys Acta,* 996, 1-6.

Lee, Y.-F., Tawfik, D. S., and Griffiths, A. D. (2002). Investigating the target recognition of DNA cytosine-5 methyltransferase HhaI by library selection using in vitro compartmentalisation (IVC). Nucleic Acids Res 30, 4937-4944.

Lim, F. (ed.). (1984) *Biomedical applications of microencapsulation.* CRC Press, Boca Raton, Fla.

Lim, F. and Sun, A. M. (1980) Micro encapsulated islets as bioartificial endocrine pancreas. *Science,* 210, 908-910.

Link, D. R., Anna, S. L., Weitz, D. A. and Stone, H. A. (2004) Geometrically mediated breakup of drops in microfluidic devices. *Phys. Rev. Letts.,* 92, 054503.

Lipinski, C. A., Lombardo, F., Dominy, B. W. and Feeney, P. J. (2001) Experimental and computational approaches to estimate solubility and permeability in drug discovery and development settings. *Adv Drug Deliv Rev,* 46, 3-26.

Lissant, K. J. (ed.). (1974) *Emulsions and emulsion technology.* Marcel Dekker, New York.

Lissant, K. J. (ed.). (1984) *Emulsions and emulsion technology.* Marcel Dekker, New York.

Lowe, K. C. (2002) Perfluorochemical respiratory gas carriers: benefits to cell culture systems. *J. Fluorine Chem.,* 118, 19-26.

Luisi, P. L. and B., S.-H. (1987) Activity and conformation of enzymes in reverse micellar solutions. *Methods Enzymol,* 136, 188-216.

Lyne, P. D. (2002). Structure-based virtual screening: an overview. Drug Discov Today 7, 1047-1055.

Mackenzie and Pinder, Dev Biol Stand. 1986; 64:181-93.

Mahajan N P, Linder K, Berry G, Gordon G W, Heim R, Herman B. Bcl-2 and Bax interactions in mitochondria probed with green fluorescent protein and fluorescence resonance energy transfer. Nat Biotechnol. June 1998; 16(6):547-52.

Mao, Q. and Walde, P. (1991) Substrate effects on the enzymatic activity of alpha-chymotrypsin in reverse micelles. *Biochem Biophys Res Commun,* 178, 1105-1112.

Mao, Q., Walde, P. and Luisi, P. L. (1992) Kinetic behaviour of alpha-chymotrypsin in reverse micelles. A stopped-flow study. *Eur J Biochem,* 208, 165-170.

Masui and Kuramitsu, Probing of DNA-binding sites of *Escherichia coli* RecA protein utilizing 1-anilinonaphthalene-8-sulfonic acid. Biochemistry. Sep. 1, 1998; 37(35): 12133-43

McDonald, J. C. and Whitesides, G. M. (2002) Poly(dimethylsiloxane) as a material for fabricating microfluidic devices. *Acc Chem Res,* 35, 491-499.

Menger, F. M. and Yamada, K. (1979) *J. Am. Chem. Soc.,* 101, 6731-6734.

Meylan, W. M. and Howard, P. H. (1995) Atom/fragment contribution method for estimating octanol-water partition coefficients. *J Pharm Sci,* 84, 83-92.

Miyawaki A, Llopis J, Heim R, McCaffery J M, Adams J A, Ikura M, Tsien R Y. Fluorescent indicators for Ca2+ based on green fluorescent proteins and calmodulin. Nature. Aug. 28, 1997; 388(6645):882-7.

Mize, P. D., Hoke, R. A., Linn, C. P., Reardon, J. E., and Schulte, T. H. (1989). Dual-enzyme cascade—an amplified method for the detection of alkaline phosphatase. Anal Biochem 179, 229-235.

Montigiani, S., Neri, G., Neri, P., and Neri, D. (1996). Alanine substitutions in calmodulin-binding peptides result in unexpected affinity enhancement. J Mol Biol 258, 6-13.

New, R. R. C. (ed.). (1990) *Liposomes: a practical approach.* Oxford University Press, Oxford.

Norman, Med Phys. November-December 1980; 7(6):609-15.

Oberholzer, T., Albrizio, M. and Luisi, P. L. (1995) Polymerase chain reaction in liposomes. *Chem Biol*, 2, 677-682.

Oberholzer, T., Wick, R., Luisi, P. L. and Biebricher, C. K. (1995) Enzymatic RNA replication in self-reproducing vesicles: an approach to a minimal cell. *Biochem Biophys Res Commun*, 207, 250-257.

Obukowicz, M. G., Turner, M. A., Wong, E. Y. and Tacon, W. C. (1988) Secretion and export of IGF-1 in *Escherichia coli* strain JM101. *Mol Gen Genet*, 215, 19-25.

Perelson, A. S., and Oster, G. F. (1979). Theoretical studies of clonal selection: minimal antibody repertoire size and reliability of self-non-self discrimination. J Theor Biol 81, 645-670.

Perez, G. M., Sanchez, F. A. and Garcia, C. F. (1992) Application of active-phase plot to the kinetic analysis of lipoxygenase in reverse micelles. *Biochem J*.

Pirrung, M. C., and Huang, C. Y. (1996). A general method for the spatially defined immobilization of biomolecules on glass surfaces using "caged" biotin. Bioconjug Chem 7, 317-321.

Qi and Grabowski, Acid beta-glucosidase: intrinsic fluorescence and conformational changes induced by phospholipids and saposin C. Biochemistry. Aug. 18, 1998; 37(33): 11544-54

Ramstrom, O., and Lehn, J. M. (2002). Drug discovery by dynamic combinatorial libraries. Nat Rev Drug Discov 1, 26-36.

Riess, J. G. (2002) Fluorous micro- and nanophases with a biomedical perspective. *Tetrahedron*, 58, 4113-4131.

Rolland, J Immunol Methods. Jan. 21, 1985; 76(1):1-10

Sadtler, V. M., Krafft, M. P. and Riess, J. G. (1996) Achieving stable, reverse water-in-fluorocarbon emulsions. *Angew. Chem. Int. Ed. Engl.*, 35, 1976-1978.

Sambrook, J., and Russell, D. W., eds. (2001). Molecular cloning: a laboratory manual (New York, Cold Spring Harbor Laboratory Press).

Savage, M. D., Mattson, G., Desai, S., Nielander, G. W., Morgensen, S., and Conklin, E. J. (1994). Avidin-biotin chemistry: a handbook, 2 edn (Rockford, Pierce Chemical Company).

Schick, M. J. (1966) *Nonionic surfactants*. Marcel Dekker, New York.

Scott, R. L. (1948) *J. Am. Chem. Soc.*, 70, 4090.

Sepp, A., Tawfik, D. S., and Griffiths, A. D. (2002). Microbead display by in vitro compartmentalisation: selection for binding using flow cytometry. FEBS Letters 532, 455-458.

Shapiro, H. M. (1995). Practical Flow Cytometry, 3 edn (New York, Wiley-Liss).

Sherman, P. (1968) *Emulsion science*. Academic Press, London.

Song, H. and Ismagilov, R. F. (2003) Millisecond kinetics on a microfluidic chip using nanoliters of reagents. *J Am Chem Soc*, 125, 14613-14619.

Song, H., Tice, J. D. and Ismagilov, R. F. (2003) A microfluidic system for controlling reaction networks in time. *Angew. Chem. Int. Ed Engl.*, 42, 767-772.

Stofko, H. R., Carr, D. W., and Scott, J. D. (1992). A single step purification for recombinant proteins. Characterization of a microtubule associated protein (MAP 2) fragment which associates with the type II cAMP-dependent protein kinase. Febs Lett 302, 274-278.

Studer, A., Hadida, S., Ferritto, R., Kim, S. Y., Jeger, P., Wipf, P. and Curran, D. P. (1997) Fluorous synthesis: a fluorous-phase strategy for improving separation efficiency in organic synthesis. *Science*, 275, 823-826.

Sun A. M., Vasek, I. and Tai, I. (1992) Microencapsulation of living cells and tissues. In Donbrow, M. (ed.), *Microencapsulation and nanoparticles in medicine and pharmacy*. CRC Press, Boca Raton, Fla., pp. 315-322.

Sundberg, S. A., Barrett, R. W., Pirrung, M., Lu, A. L., Kiangsoontra, B., and Holmes, C. P. (1995). Spatially-addressable immobilisation of macromolecules on solid supports. J Am Chem Soc 117, 12050-12057.

Tawfik, D. S., and Griffiths, A. D. (1998). Man-made cell-like compartments for molecular evolution. Nat Biotechnol 16, 652-656.

Thorsen, T., R. W., R., Arnold, F. H. and Quake, S. R. (2001) Dynamic pattern formation in a vesicle-generating microfluidic device. *Phys. Rev. Letts.*, 86, 4163-4166.

Tripet, B., Yu, L., Bautista, D. L., Wong, W. Y., Irvin, R. T., and Hodges, R. S. (1996). Engineering a de novo-designed coiled-coil heterodimerization domain off the rapid detection, purification and characterization of recombinantly expressed peptides and proteins. Protein Eng 9, 1029-1042.

Umbanhowar, P. B., Prasad, V. and Weitz, D. A. (2000) Monodisperse emulsions generated via drop break off in a coflowing steam. *Langmuir*, 16, 347-351.

van Hal, D. A., Bouwstra, J. A. and Junginger, H. E. (1996) Nonionic surfactant vesicles containing estradiol for topical application. In Benita, S. (ed.), *Microencapsulation: methods and industrial applications*. Marcel Dekker, New York, pp. 329-347.

Voss E W Jr. Kinetic measurements of molecular interactions by spectrofluorometry. J Mol Recognit. June 1993; 6(2): 51-8

Walde, P., Goto, A., Monnard, P.-A., Wessicken, M. and Luisi, P. L. (1994) Oparin's reactions revisited: enzymatic synthesis of poly(adenylic acid) in micelles and self-reproducing vesicles. *J. Am. Chem. Soc.*, 116, 7541-7547.

Walde, P., Han, D. and Luisi, P. L. (1993) Spectroscopic and kinetic studies of lipases solubilized in reverse micelles. *Biochemistry*, 32, 4029-4034.

Walde, P., Peng, Q., Fadnavis, N. W., Battistel, E. and Luisi, P. L. (1988) Structure and activity of trypsin in reverse micelles. *Eur J Biochem*, 173, 401-409.

Whateley, T. L. (1996) Microcapsules: preparation by interfacial polymerisation and interfacial complexation and their applications. In Benita, S. (ed.), *Microencapsulation: methods and industrial applications*. Marcel Dekker, New York, pp. 349-375.

Wick, R. and Luisi, P. L. (1996) Enzyme-containing liposomes can endogenously produce membrane-constituting lipids. *Chem Biol*, 3, 277-285.

Zhang, Z. Y., Thieme-Sefler, A. M., Maclean, D., McNamara, D. J., Dobrusin, E. M., Sawyer, T. K., and Dixon, J. E. (1993). Substrate specificity of the protein tyrosine phosphatases. Proc Natl Acad Sci USA 90, 4446-4450.

All publications mentioned in the above specification, and references cited in said publications, are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method of forming a small molecule compound comprising:
   providing at least a first aqueous fluid comprising at least a first small molecule compound having a molecular weight of less than 500 Daltons wherein said first small molecule compound is an amine with a difluoromethylene phosphonate moiety;
   providing at least a second aqueous fluid comprising at least a second small molecule compound having a molecular weight of less than 500 Daltons wherein said second small molecule compound is an aldehyde with a difluoromethylene phosphonate moiety;
   encapsulating said at least first small molecule compound into at least a first aqueous microcapsule within an immiscible fluorocarbon oil:
   encapsulating said at least second small molecule compound into at least a second aqueous microcapsule within an immiscible fluorocarbon oil; and
   fusing said at least first and said at least second aqueous microcapsules, thereby causing a chemical reaction between said at least first and at least second small molecule compounds to form at least a third small molecule compound.

2. The method of claim 1, wherein said at least first small molecule compound is attached to a microbead.

3. The method of claim 1, wherein said at least second small molecule compound is attached to a microbead.

4. The method of claim 1, further comprising isolating said at least third small molecule compound.

5. The method of claim 1, further comprising identifying said at least third small molecule compound.

6. The method of claim 5, wherein said at least third small molecule compound is identified by its optical properties.

7. The method of claim 1, wherein said at least first small molecule compound comprises at least a first label and said at least second small molecule compound comprises at least a second label, wherein said at least first and said at least second labels are different.

8. The method of claim 1, wherein said at least second aqueous microcapsule comprises no more than one said at least second small molecule compound.

* * * * *